US010245024B2

(12) United States Patent
Kostrzewski

(10) Patent No.: US 10,245,024 B2
(45) Date of Patent: *Apr. 2, 2019

(54) STITCHING END EFFECTOR

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/271,831

(22) Filed: Sep. 21, 2016

(65) Prior Publication Data

US 2017/0007235 A1  Jan. 12, 2017

Related U.S. Application Data

(63) Continuation of application No. 14/507,900, filed on Oct. 7, 2014, now Pat. No. 9,468,434.

(60) Provisional application No. 62/006,922, filed on Jun. 3, 2014.

(51) Int. Cl.
| | | |
|---|---|---|
| *A61B 17/04* | (2006.01) | |
| *A61B 17/00* | (2006.01) | |
| *A61B 17/06* | (2006.01) | |

(52) U.S. Cl.
CPC .... *A61B 17/0469* (2013.01); *A61B 17/00234* (2013.01); *A61B 17/0491* (2013.01); *A61B 2017/0472* (2013.01); *A61B 2017/0608* (2013.01)

(58) Field of Classification Search
CPC . A61B 17/04; A61B 17/0469; A61B 17/0482; A61B 17/0491; A61B 2017/0472; A61B 2017/0496
See application file for complete search history.

(56) References Cited

U.S. PATENT DOCUMENTS

| | | | |
|---|---|---|---|
| 1,822,330 | A | 9/1931 | Ainslie |
| 2,327,353 | A | 8/1943 | Karle |
| 3,073,311 | A | 1/1963 | Tibbs et al. |
| 3,123,077 | A | 3/1964 | Alcamo |
| 4,236,470 | A | 12/1980 | Stenson |
| 4,417,532 | A | 11/1983 | Yasukata |

(Continued)

FOREIGN PATENT DOCUMENTS

| | | |
|---|---|---|
| DE | 4423881 C1 | 10/1995 |
| EP | 0592244 A2 | 4/1994 |

(Continued)

OTHER PUBLICATIONS

European Search Report dated Oct. 7, 2015, issued in European Application No. 15167797.

(Continued)

*Primary Examiner* — Ryan J. Severson

(57) ABSTRACT

A stitching assembly includes upper and lower cradles, upper and lower needles, and first and second sutures supported by the upper and lower needles, respectively. The cradles move along a curved path in relation to the carriages between advanced and retracted positions. When each cradle is moved from the retracted position towards the advanced position, a stitch loop is formed when the respective needle is retracted. This process is repeated alternating between the first and second cradles with the upper and lower needles passing through the previous stitch loop formed by the other needle before passing through the tissue.

20 Claims, 22 Drawing Sheets

(56) References Cited

U.S. PATENT DOCUMENTS

| | | |
|---|---|---|
| 4,890,615 A | 1/1990 | Caspari et al. |
| 4,923,461 A | 5/1990 | Caspari et al. |
| 4,935,027 A | 6/1990 | Yoon |
| 5,037,433 A | 8/1991 | Wilk et al. |
| 5,042,707 A | 8/1991 | Taheri |
| 5,080,663 A | 1/1992 | Mills et al. |
| 5,100,421 A | 3/1992 | Christoudias |
| 5,100,430 A | 3/1992 | Avellanet et al. |
| 5,209,747 A | 5/1993 | Knoepfler |
| 5,271,543 A | 12/1993 | Grant et al. |
| 5,300,082 A | 4/1994 | Sharpe et al. |
| 5,308,353 A | 5/1994 | Beurrier |
| 5,314,445 A | 5/1994 | Heidmueller Nee Degwitz et al. |
| 5,330,502 A | 7/1994 | Hassler et al. |
| 5,336,229 A | 8/1994 | Noda |
| 5,350,391 A | 9/1994 | Iacovelli |
| 5,358,498 A | 10/1994 | Shave |
| 5,364,408 A | 11/1994 | Gordon |
| 5,374,275 A | 12/1994 | Bradley et al. |
| 5,374,277 A | 12/1994 | Hassler |
| 5,387,221 A | 2/1995 | Bisgaard |
| 5,389,103 A | 2/1995 | Melzer et al. |
| 5,391,176 A | 2/1995 | de la Torre |
| 5,403,342 A | 4/1995 | Tovey et al. |
| 5,405,352 A | 4/1995 | Weston |
| 5,439,478 A | 8/1995 | Palmer |
| 5,454,823 A | 10/1995 | Richardson et al. |
| 5,454,827 A | 10/1995 | Aust et al. |
| 5,458,609 A | 10/1995 | Gordon et al. |
| 5,462,560 A | 10/1995 | Stevens |
| 5,472,446 A | 12/1995 | de la Torre |
| 5,478,344 A | 12/1995 | Stone et al. |
| 5,480,406 A | 1/1996 | Nolan et al. |
| 5,496,334 A | 3/1996 | Klundt et al. |
| 5,527,323 A | 6/1996 | Jervis et al. |
| 5,540,703 A | 7/1996 | Barker, Jr. et al. |
| 5,540,704 A | 7/1996 | Gordon et al. |
| 5,540,706 A | 7/1996 | Aust et al. |
| 5,549,617 A | 8/1996 | Green et al. |
| 5,549,637 A | 8/1996 | Crainich |
| 5,562,686 A | 10/1996 | Sauer et al. |
| 5,564,615 A | 10/1996 | Bishop et al. |
| 5,571,090 A | 11/1996 | Sheds |
| 5,573,286 A | 11/1996 | Rogozinski |
| 5,575,799 A | 11/1996 | Bolanos et al. |
| 5,575,800 A | 11/1996 | Gordon |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,628,756 A | 5/1997 | Barker, Jr. et al. |
| 5,630,825 A | 5/1997 | de la Torre et al. |
| 5,632,751 A | 5/1997 | Piraka |
| 5,643,293 A | 7/1997 | Kogasaka et al. |
| 5,643,294 A | 7/1997 | Tovey et al. |
| 5,662,664 A | 9/1997 | Gordon et al. |
| 5,662,666 A | 9/1997 | Onuki et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,690,653 A | 11/1997 | Richardson et al. |
| 5,700,272 A | 12/1997 | Gordon et al. |
| 5,702,408 A | 12/1997 | Wales et al. |
| 5,715,942 A | 2/1998 | Li et al. |
| 5,728,107 A | 3/1998 | Zlock et al. |
| 5,728,109 A | 3/1998 | Schulze et al. |
| 5,728,113 A | 3/1998 | Sherts |
| 5,730,747 A | 3/1998 | Ek et al. |
| 5,741,277 A | 4/1998 | Gordon et al. |
| 5,746,751 A | 5/1998 | Sherts |
| 5,749,898 A | 5/1998 | Schulze et al. |
| 5,752,973 A | 5/1998 | Kieturakis |
| 5,755,729 A | 5/1998 | de la Torre et al. |
| 5,759,188 A | 6/1998 | Yoon |
| 5,766,196 A | 6/1998 | Griffiths |
| 5,779,646 A | 7/1998 | Koblish et al. |
| 5,792,153 A | 8/1998 | Swain et al. |
| 5,792,165 A | 8/1998 | Klieman et al. |
| 5,797,537 A | 8/1998 | Oberlin et al. |
| 5,797,927 A | 8/1998 | Yoon |
| 5,797,928 A | 8/1998 | Kogasaka |
| 5,814,054 A | 9/1998 | Kortenbach et al. |
| 5,814,069 A | 9/1998 | Schulze et al. |
| 5,817,119 A | 10/1998 | Klieman et al. |
| 5,827,323 A | 10/1998 | Klieman et al. |
| 5,843,126 A | 12/1998 | Jameel |
| 5,860,990 A | 1/1999 | Nobles et al. |
| 5,865,836 A | 2/1999 | Miller |
| 5,871,488 A | 2/1999 | Tovey et al. |
| 5,876,412 A | 3/1999 | Piraka |
| 5,893,592 A | 4/1999 | Schulze et al. |
| 5,897,563 A | 4/1999 | Yoon et al. |
| 5,906,630 A | 5/1999 | Anderhub et al. |
| 5,908,428 A | 6/1999 | Scirica et al. |
| 5,911,727 A | 6/1999 | Taylor |
| 5,928,136 A | 7/1999 | Barry |
| 5,931,855 A | 8/1999 | Buncke |
| 5,938,668 A | 8/1999 | Scirica et al. |
| 5,941,430 A | 8/1999 | Kuwabara |
| 5,947,982 A | 9/1999 | Duran |
| 5,947,983 A | 9/1999 | Solar et al. |
| 5,954,731 A | 9/1999 | Yoon |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon et al. |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,277,132 B1 | 8/2001 | Brhel |
| 6,319,262 B1 | 11/2001 | Bates et al. |
| 6,332,889 B1 | 12/2001 | Sancoff et al. |
| 6,346,111 B1 | 2/2002 | Gordon et al. |
| 6,358,259 B1 | 3/2002 | Swain et al. |
| 6,494,888 B1 | 12/2002 | Laufer |
| 6,506,196 B1 | 1/2003 | Laufer |
| 6,517,539 B1 | 2/2003 | Smith et al. |
| 6,533,795 B1 | 3/2003 | Tran et al. |
| 6,533,796 B1 | 3/2003 | Sauer et al. |
| 6,562,052 B2 | 5/2003 | Nobles et al. |
| 6,569,105 B1 | 5/2003 | Kortenbach et al. |
| 6,582,450 B2 | 6/2003 | Ouchi |
| 6,596,015 B1 | 7/2003 | Pitt et al. |
| 6,599,310 B2 | 7/2003 | Leung et al. |
| 6,638,287 B2 | 10/2003 | Danitz |
| 6,663,639 B1 | 12/2003 | Laufer |
| 6,663,641 B1 | 12/2003 | Kovac et al. |
| 6,666,854 B1 | 12/2003 | Lange |
| 6,676,676 B2 | 1/2004 | Danitz |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |

(56) References Cited

U.S. PATENT DOCUMENTS

| | | |
|---|---|---|
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer |
| 6,889,116 B2 | 5/2005 | Jinno |
| 6,911,034 B2 | 6/2005 | Nobles et al. |
| 6,936,054 B2 | 8/2005 | Chu |
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,011,668 B2 | 3/2006 | Sancoff et al. |
| 7,033,370 B2 | 4/2006 | Gordon et al. |
| 7,037,315 B2 | 5/2006 | Sancoff et al. |
| 7,041,111 B2 | 5/2006 | Chu |
| 7,052,489 B2 | 5/2006 | Griego et al. |
| RE39,152 E | 6/2006 | Aust et al. |
| 7,060,077 B2 | 6/2006 | Gordon et al. |
| 7,063,710 B2 | 6/2006 | Takamoto et al. |
| 7,063,715 B2 | 6/2006 | Onuki et al. |
| 7,090,686 B2 | 8/2006 | Nobles et al. |
| 7,107,124 B2 | 9/2006 | Green |
| 7,153,314 B2 | 12/2006 | Laufer |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 8,197,510 B2 | 6/2012 | Nobles |
| 8,292,903 B2 | 10/2012 | Dreyfus et al. |
| 8,348,962 B2 | 1/2013 | Nobles et al. |
| 8,747,424 B2 | 6/2014 | Taylor et al. |
| 9,468,434 B2 | 10/2016 | Kostrzewski |
| 2001/0023352 A1 | 9/2001 | Gordon et al. |
| 2002/0010480 A1 | 1/2002 | Sancoff et al. |
| 2002/0045908 A1 | 4/2002 | Nobles et al. |
| 2002/0049453 A1 | 4/2002 | Nobles et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2003/0233107 A1 | 12/2003 | Gellman et al. |
| 2003/0233108 A1 | 12/2003 | Gellman et al. |
| 2004/0006352 A1 | 1/2004 | Nobles et al. |
| 2004/0010245 A1 | 1/2004 | Cerier et al. |
| 2004/0059350 A1 | 3/2004 | Gordon et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0088003 A1 | 5/2004 | Leung et al. |
| 2004/0092963 A1 | 5/2004 | Moll et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0228407 A1 | 10/2005 | Nobles et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0052801 A1 | 3/2006 | Dreyfuss et al. |
| 2006/0069396 A1 | 3/2006 | Meade et al. |
| 2006/0111209 A1 | 5/2006 | Hinman et al. |
| 2006/0235304 A1 | 10/2006 | Harhen et al. |
| 2006/0253126 A1 | 11/2006 | Bjerken et al. |
| 2006/0282091 A1 | 12/2006 | Shelton et al. |
| 2006/0282093 A1 | 12/2006 | Shelton et al. |
| 2007/0005110 A1 | 1/2007 | Collier et al. |
| 2007/0043385 A1 | 2/2007 | Nobles et al. |
| 2007/0276413 A1 | 11/2007 | Nobles |
| 2008/0071296 A1 | 3/2008 | Klundt et al. |
| 2008/0188868 A1 | 8/2008 | Weitzner et al. |
| 2008/0312688 A1 | 12/2008 | Nawrocki et al. |
| 2009/0312773 A1 | 12/2009 | Cabrera et al. |
| 2010/0268256 A1 | 10/2010 | Dreyfuss et al. |
| 2012/0283754 A1 | 11/2012 | Murillo et al. |
| 2012/0310220 A1 | 12/2012 | Malkowski et al. |
| 2013/0030450 A1 | 1/2013 | Dreyfuss et al. |
| 2013/0317525 A1 | 11/2013 | Wingardner, III et al. |
| 2014/0296880 A1 | 10/2014 | Heneveld |
| 2014/0350576 A1 | 11/2014 | Patel et al. |
| 2015/0327850 A1 | 11/2015 | Kostrzewski |
| 2015/0342599 A1 | 12/2015 | Kostrzewski |

FOREIGN PATENT DOCUMENTS

| | | |
|---|---|---|
| EP | 0647431 A2 | 4/1995 |
| EP | 1481628 A1 | 12/2004 |
| EP | 1915957 A2 | 4/2008 |
| EP | 1915966 A1 | 4/2008 |
| EP | 2044890 A1 | 4/2009 |
| EP | 2133028 A2 | 12/2009 |
| EP | 2329773 A1 | 6/2011 |
| EP | 2586382 A2 | 5/2013 |

(56) References Cited

FOREIGN PATENT DOCUMENTS

| EP | 2606834 A2 | 6/2013 |
|---|---|---|
| WO | 8705122 A1 | 8/1987 |
| WO | 9727807 A1 | 8/1997 |
| WO | 9811814 A2 | 3/1998 |
| WO | 9811829 A1 | 3/1998 |
| WO | 9853745 A1 | 12/1998 |
| WO | 9915090 A1 | 4/1999 |
| WO | 9918859 A1 | 4/1999 |
| WO | 0067834 A1 | 11/2000 |
| WO | 0174254 A1 | 10/2001 |
| WO | 0234147 A1 | 5/2002 |
| WO | 03017850 A2 | 3/2003 |
| WO | 2006061868 A1 | 6/2006 |
| WO | 2008042423 A2 | 4/2008 |
| WO | 2008045333 A2 | 4/2008 |

OTHER PUBLICATIONS

Feiss, Carl, "Universal S 3B Stand", Sep. 15, 2006, XP055216369, http://www.ophthalword.decosmoshop/pix/a/media/28072015/ Zeiss S3 Floor Stand User Manual.pdf.

U.S. Appl. No. 14/279,928, filed May 16, 2014, inventor: Stanislaw Kostrzewski.

European Search Report dated Sep. 3, 2015, issued in EP Application No. 15170195.

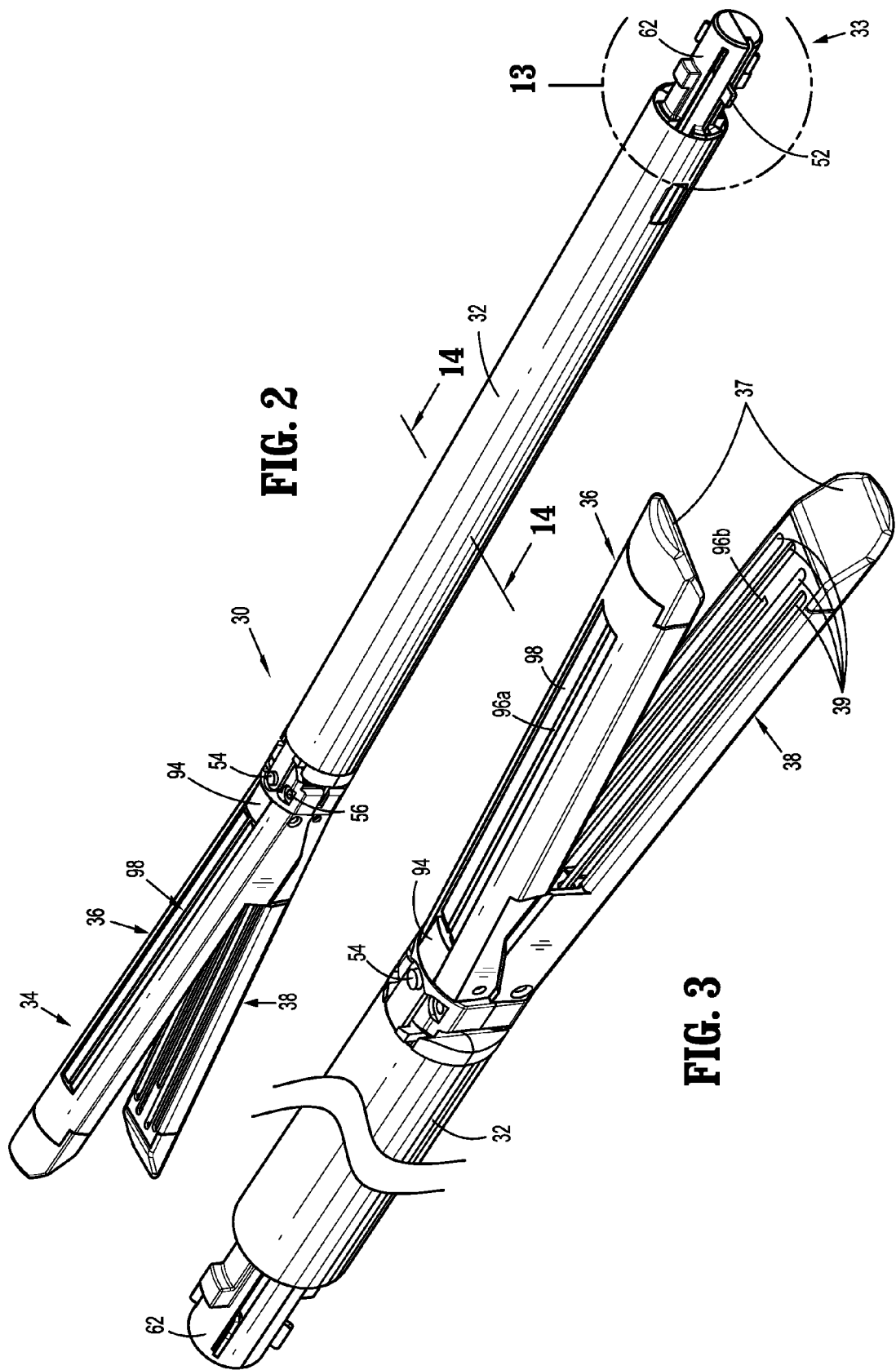

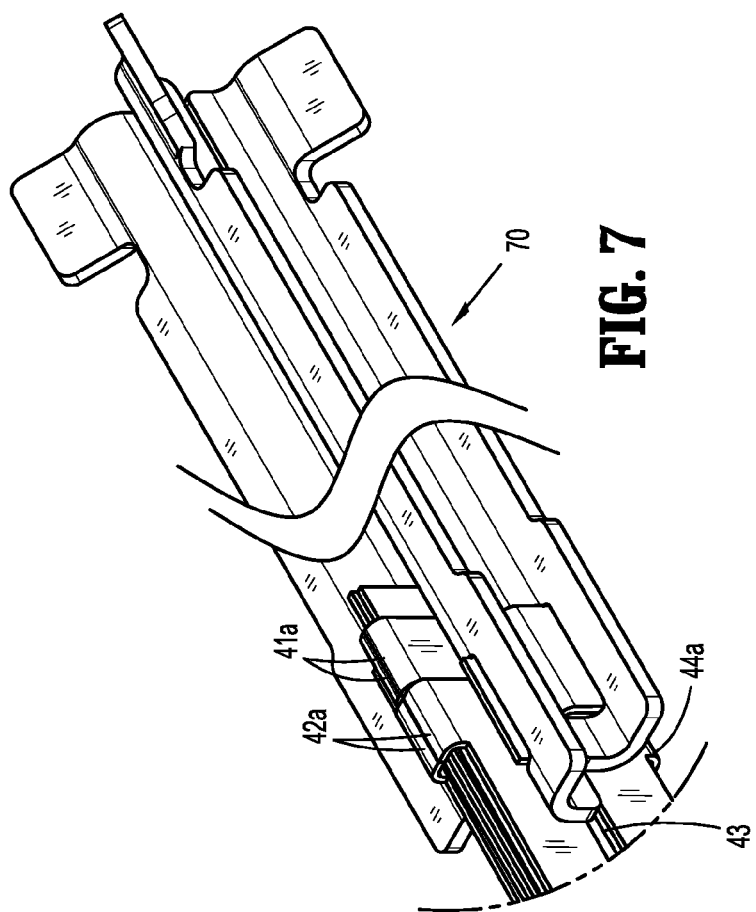
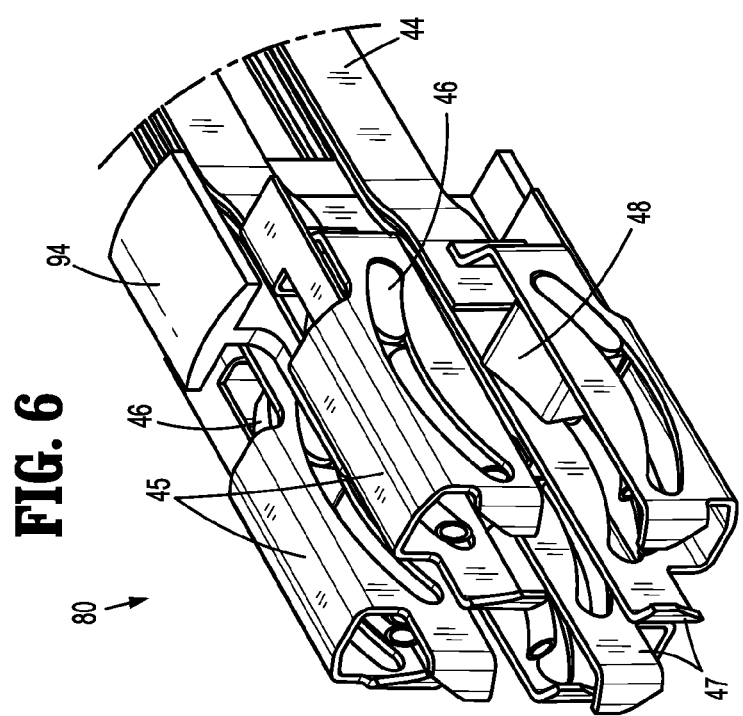

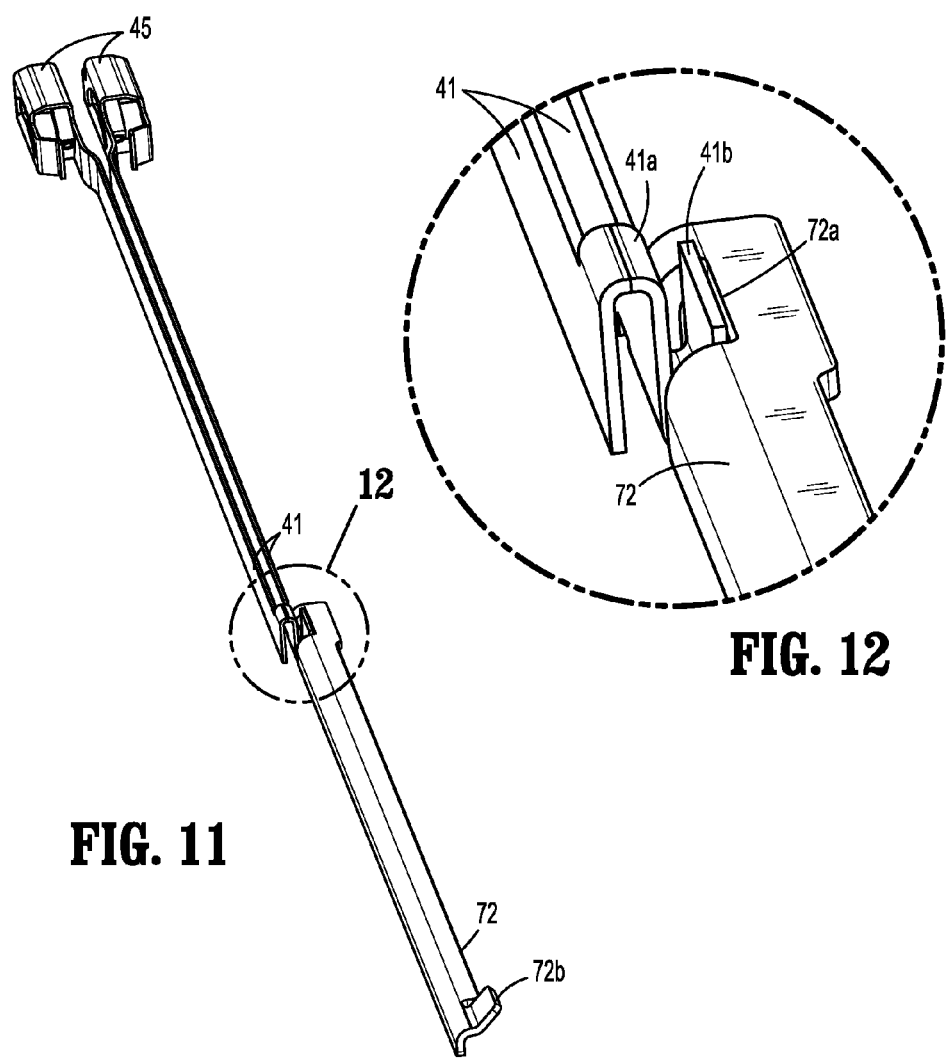
FIG. 11
FIG. 12
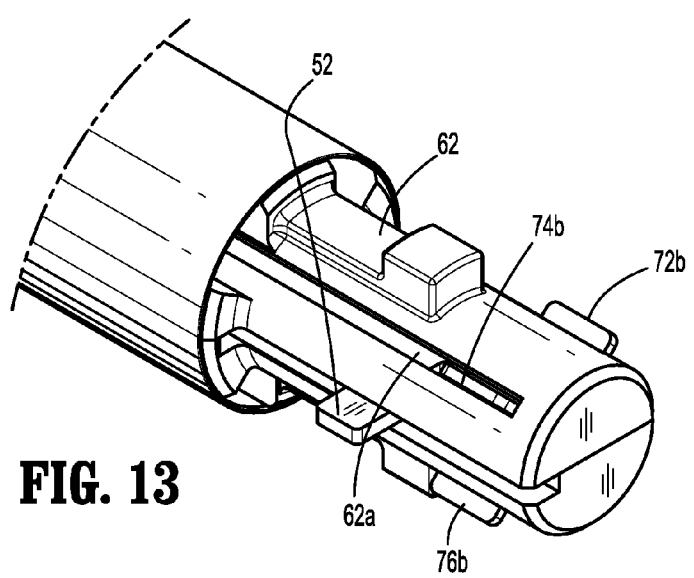
FIG. 13

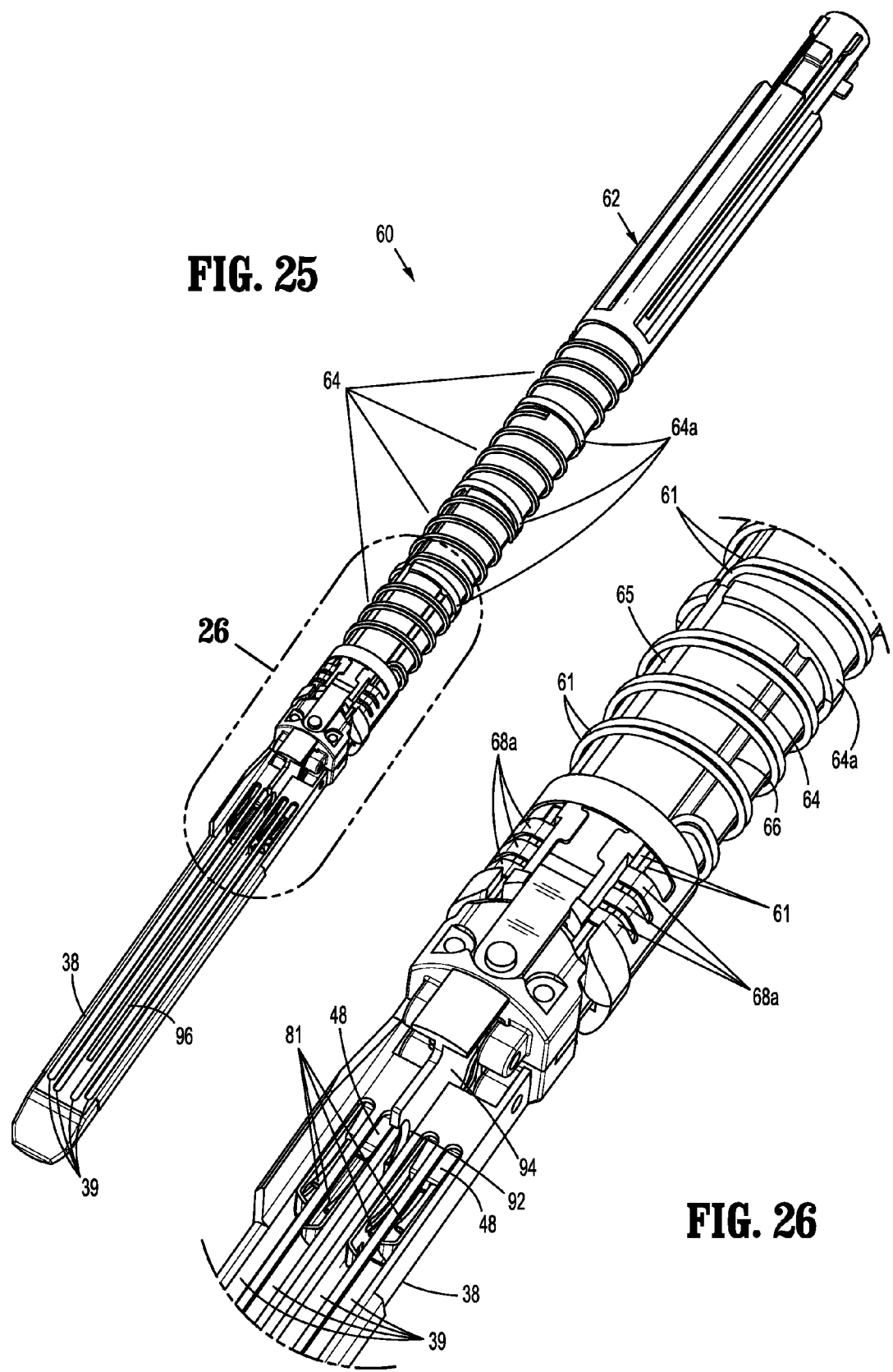

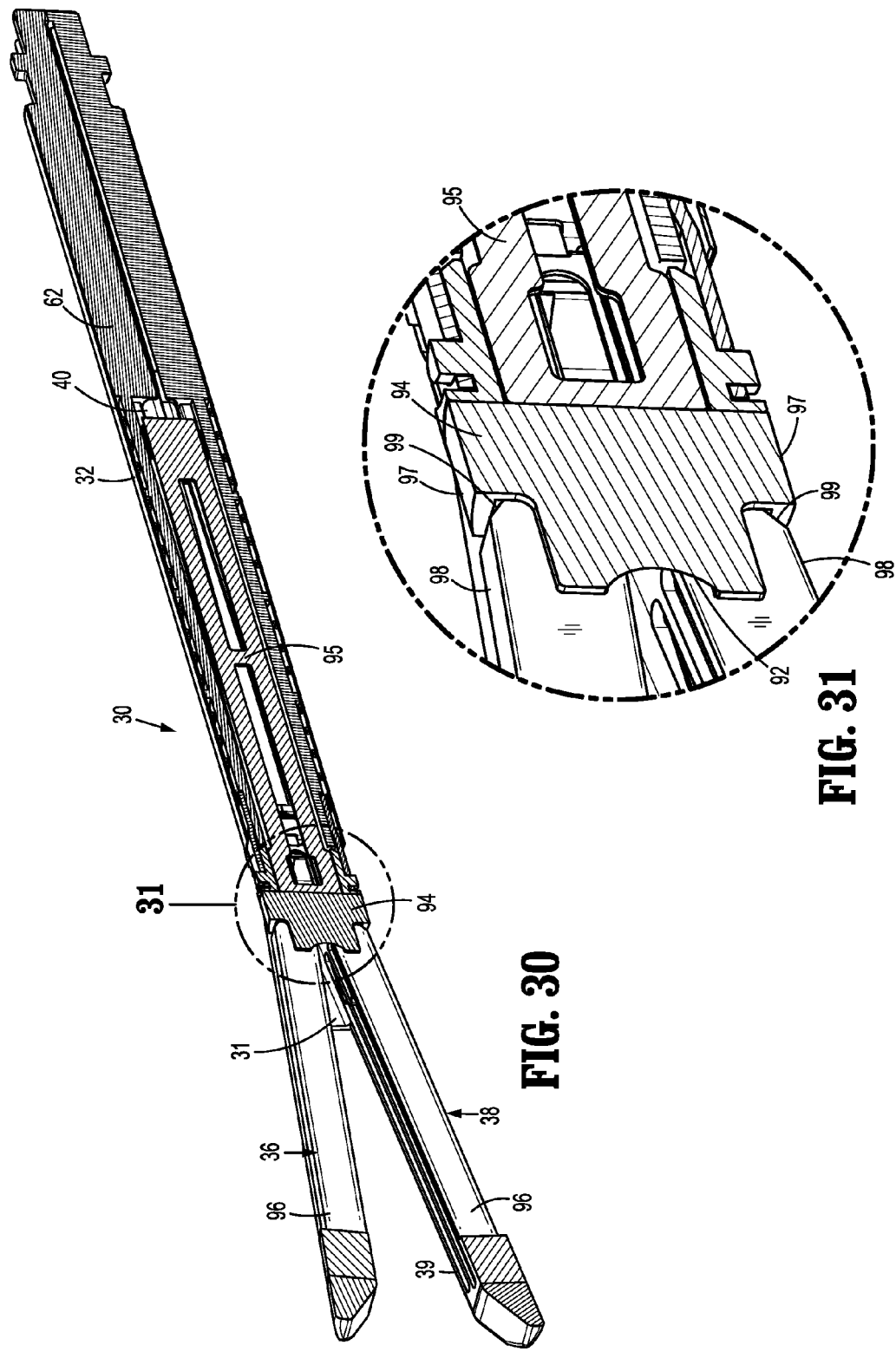

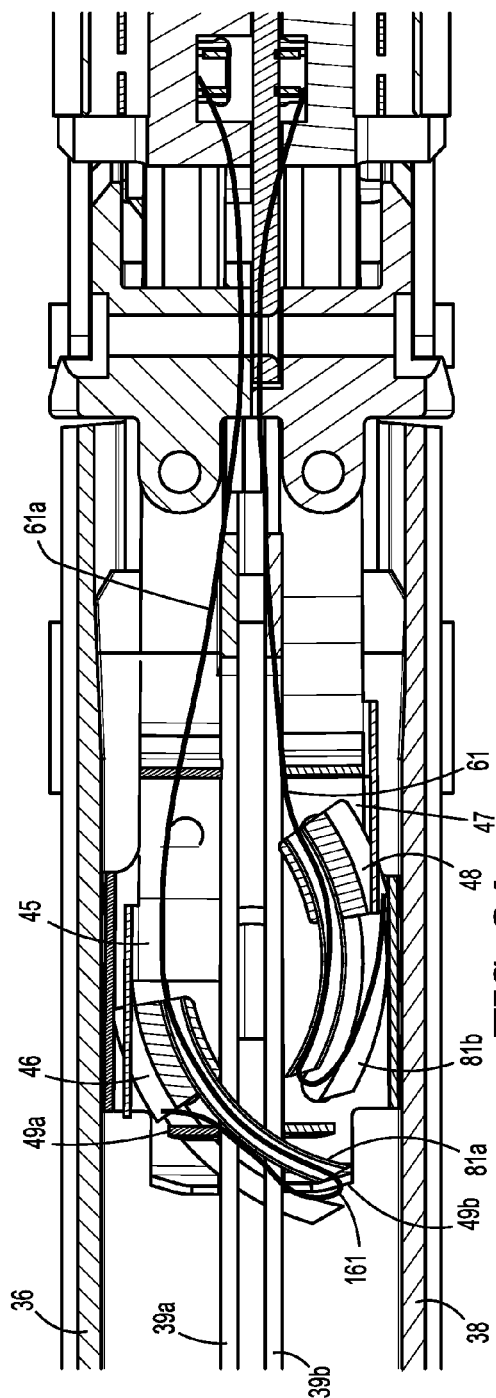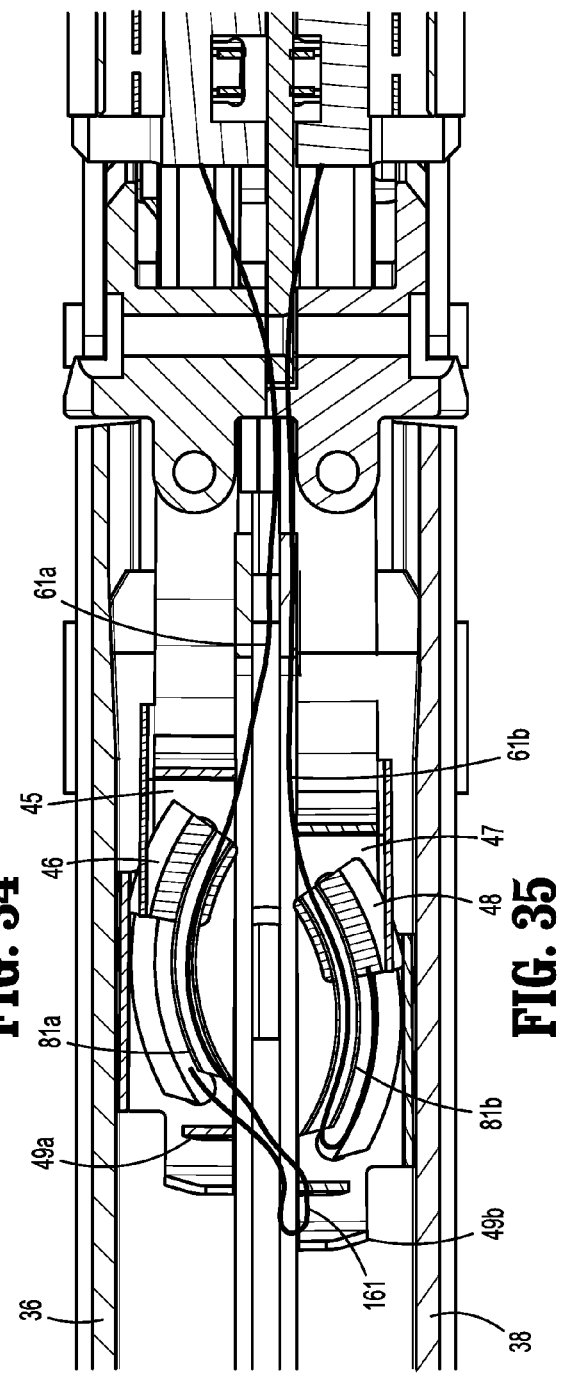

STITCHING END EFFECTOR

CROSS-REFERENCE TO RELATED APPLICATIONS

This application is a continuation of U.S. patent application Ser. No. 14/507,900, filed Oct. 7, 2014, which claims the benefit of and priority to U.S. Provisional Patent Application Ser. No. 62/006,922, filed Jun. 3, 2014. The entire disclosure of each of the above applications is incorporated by reference herein.

BACKGROUND

1. Technical Field

The present disclosure relates to surgical instruments, specifically, surgical instruments with a stitching end effector for forming stitches.

2. Background of the Invention

As medical and hospital costs continue to increase, surgeons are constantly striving to develop advanced surgical techniques. Advances in the surgical field are often related to the development of operative techniques which involve less invasive surgical procedures which reduce overall patient trauma. In this manner, the length of hospital stays and thus, medical costs can be significantly reduced.

One of the truly great advances to reduce the invasiveness of surgical procedures is endoscopic surgery. Endoscopic surgery involves surgery through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, it is often necessary to suture body organs or tissue. Traditionally, suturing was accomplished by hand using a needle attached to a suture material. This procedure required open access to the tissue to be sutured. Upon the advent of endoscopic surgical procedures, endoscopic suturing instruments have been developed. The development of endoscopic suturing instruments is especially challenging because of the small openings through which the suturing of body organs or tissues must be accomplished.

SUMMARY

In an aspect of the present disclosure, a stitching assembly includes an upper cradle, an upper carriage, an upper needle, and a first suture. The upper carriage is configured to support the upper cradle for movement along a curved path between an advanced position and a retracted position relative to the upper carriage. The upper needle is supported by and extends distally from the upper cradle. The first suture is supported by the upper needle. The upper cradle and the upper carriage are configured to draw the first suture through tissue when the upper cradle is moved towards the advanced position and are configured to form a first stitch loop in the first suture when the upper cradle is moved from the advanced position towards the retracted position. In addition, the stitching assembly includes a lower cradle, a lower carriage, a lower needle, and a second suture. The lower carriage is configured to support the lower cradle for movement along a curved path between an advanced position and a retracted position relative to the lower carriage. The lower needle is supported by and extends distally from the lower cradle. The second suture is supported by the lower needle. The lower cradle and the lower carriage are configured to draw the first suture through tissue and the first stitch loop when the lower cradle is moved towards the advanced position and are configured to form a second stitch loop in the second suture when the lower cradle is moved from the advanced position towards the retracted position.

In aspects, the upper needle includes an outer surface and a distal end and the upper carriage includes an upper plow that is positioned adjacent the distal end of the upper needle. The upper plow of the upper carriage and the outer surface of the upper needle being configured to capture a portion of the first suture therebetween as the upper cradle is moved towards the advanced position. In addition, the lower needle includes an outer surface and a distal end and the lower carriage includes a lower plow that is positioned adjacent the distal end of the lower needle. The lower plow of the lower carriage and the outer surface of the lower needle being configured to capture a portion of the second suture therebetween as the lower cradle is moved towards the advanced position.

In some aspects, the upper carriage has a sidewall that defines a cam slot and the upper cradle includes a sidewall including a cam. The cam of the upper cradle is received within the cam slot of the upper carriage. The upper needle may be a curved needle. The cam slot of the upper carriage may be a curved cam slot defining the curved path of the upper cradle. A curvature of the curved path of the upper cradle may correspond to a curvature of the curved upper needle.

In another aspect of the present disclosure, a stitching loading unit includes an inner housing, a jaw member assembly, and a stitching assembly. The inner housing having proximal and distal ends. The jaw member assembly is positioned at the distal end of the inner housing and includes first and second jaw members. The first and second jaw members are moveable relative to one another between open and clamped positions. Each of the first and second jaw members define a longitudinal needle slot positioned parallel to the longitudinal axis of the jaw member. The stitching assembly may be any of the stitching assemblies disclosed herein.

In aspects, the stitching loading unit includes a suture storage and delivery assembly having a suture tension, a first suture recess, a second suture recess, a groove, a conduit, a portion of the first suture, and a portion of the second suture. The first suture recess is defined by and along a length of the inner housing, the first suture recess is positioned proximal to the suture tensioner. The second suture recess is defined by and along a length of the inner housing proximal to the first suture recess. The groove is defined in the inner housing through the first suture recess and into the second suture recess. The conduit is disposed within the groove. The portion of the first suture is wound around the inner housing in the first suture recess, passes through the suture tensioner, and through the upper needle. The portion of the second suture is wound around the inner housing in the second suture recess, passes through the conduit, passes through the suture tensioner, and passes through the lower needle.

In some aspects, the stitching loading unit includes a drive bar assembly that is disposed within the inner housing. The drive bar assembly includes an upper carriage drive bar, an upper cradle drive bar, a lower carriage drive bar, and a lower cradle drive bar. The upper carriage drive bar includes a distal end that is connected to the upper carriage to move the upper carriage within the upper jaw member. The upper cradle drive bar includes a distal end that is operatively associated with the upper cradle to move the upper cradle between the retracted and advanced positions. The lower carriage drive bar includes a distal end that is connected to the lower carriage to move the lower carriage within the lower jaw member. The lower cradle drive bar includes a distal end that is operatively associated with the lower cradle to move the lower cradle between the retracted and advanced positions. A proximal end of the upper cradle drive bar may be disposed over the upper carriage drive bar distal to a proximal end of the upper carriage drive bar such that the upper cradle is advanced with the upper carriage. A proximal end of the lower cradle drive bar may be disposed over the lower carriage drive bar distal to a proximal end of the lower carriage drive bar such that the lower cradle is advanced with the lower carriage.

In particular aspects, the distal end of the upper cradle drive bar includes a cradle finger that is operatively associated with the upper cradle. In embodiments, the cradle drive finger is flexible. A distal end of the cradle drive finger may be fixed to a surface of the upper cradle such that when the cradle is in the advanced position, the cradle drive finger forms a curve with a surface of the upper cradle. In other embodiments, the cradle drive finger is substantially rigid. The cradle drive finger may include a toothed rack and a surface of the upper cradle may include a pinion. The toothed rack engages the pinion to move the cradle between the retracted and advanced positions.

In certain aspects, the stitching loading unit includes an extension rod assembly disposed within the inner housing. The extension rod assembly including an upper carriage extension rod, an upper cradle extension rod, a lower carriage extension rod, and a lower cradle extension rod. The upper carriage extension rod includes a distal end that is operatively associated with the upper carriage drive bar to longitudinally translate the upper carriage drive bar. The upper cradle extension rod includes a distal end that is operatively associated with the upper cradle drive bar to longitudinally translate the upper cradle drive bar. The lower carriage extension rod includes a distal end that is operatively associated with the lower carriage drive bar to longitudinally translate the lower carriage drive bar. The lower cradle extension rod includes a distal end that is operatively associated with the lower cradle drive bar to longitudinally translate the lower cradle drive bar.

In aspects, the stitching loading unit includes including an I-beam, and a knife defined by the I-beam. The I-beam is positioned within and is longitudinally translatable within a knife slot. The knife slot is defined about the longitudinal axis of each of the first and second jaw members. The knife slot extends from the proximal end of each of the first and second jaw members and towards a distal end of each of the first and second jaw members. The drive bar assembly may include a knife drive bar that has a proximal end connected to the upper carriage drive bar. A distal end of the knife drive bar is operatively associated with the I-beam to advance the I-beam with the upper carriage drive bar. The first and second jaw members each define a beam groove in an outer surface of the jaw member. The I-beam may include upper and lower flanges integrally formed on upper and lower surfaces thereof. The upper and lower flanges may be received within the beam grooves of the upper and lower jaw member to urge the jaw members towards the clamped position as the I-beam is advanced through the knife slot.

In some aspects, the stitching loading unit includes an articulation assembly having an articulation joint, an articulation pivot, an articulation rod, and an articulation pin. The articulation joint is positioned between a proximal end of the jaw member assembly and a distal end of the inner housing. The articulation pivot passes through the articulation joint. The articulation pivot is orthogonal to and passes through the longitudinal axis of the first and second jaw members when the jaw members are in the clamped position. The articulation rod is disposed within the inner housing and includes a proximal end. The articulation pin passes through the proximal end of the articulation rod and the articulation joint. The articulation pin is parallel to the articulation pivot. The articulation joint is offset from the articulation pivot such that when the articulation rod is longitudinally translated, the jaw member assembly articulates relative to the outer tube about the articulation pivot.

In still another aspect of the present disclosure, a surgical instrument for suturing tissue includes a handle and a stitching loading unit. The stitching loading unit is operatively associated with the handle. The stitching loading unit may be any of the stitching loading units disclosed herein.

In aspects, the handle includes a drive shaft for manipulating the stitching loading unit. The surgical instrument may include an adaptor having proximal and distal ends. The proximal end of the adaptor engages the handle and the distal end of the adaptor receives a connector of the stitching loading unit. The connector is configured to manipulate the stitching assembly of the stitching loading unit. The adaptor is configured to convert rotation of drive shafts of the handle to longitudinal translation to longitudinal translation of the stitching assembly of the stitching loading unit.

In still yet another aspect of the present disclosure, a stitching assembly includes a first jaw member, a second jaw member, a first needle, a first suture, a second needle, and a second suture. The first jaw member has proximal and distal ends and the second jaw member has proximal and distal ends. The first needle is moveable in a stepwise manner between the proximal and distal ends of the first jaw member. The first needle is moveable between a retracted position, where the first needle is disposed within the first jaw member, and an advanced position, where the first needle is extended towards the second jaw member from the first jaw member. The first suture is associated with the first needle. The second needle is moveable in a stepwise manner between the proximal and distal ends of the second jaw member. The second needle is moveable between a retracted position, where the second needle is disposed within the second jaw member, and an advanced position, where the second needle is extended towards the first jaw member from the second jaw member. The second suture is associated with the second needle. In addition, the stitching assembly includes first and second drive bars. The first drive bar is configured at each step of movement of the first needle to move the first needle from the retracted position to the advanced position and to return the first needle to the retracted position. This movement of the first needle forms a suture loop in the first suture through tissue and adjacent the second jaw member. The second drive bar is configured to at each step of movement of the second needle to move the second needle from the retracted position to the advanced position and to return the second needle to the retracted position. This movement of the second needle forms a suture loop in the second suture through tissue and adjacent the first jaw member.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, wherein:

FIG. 2 is a rear perspective view of the stitching end effector of FIG. 1 with the jaws in an open position;

FIG. 3 is a front perspective view of the stitching end effector of FIG. 2 with the jaws in an open position;

FIG. 6 is an enlarged view of the indicated area of detail of FIG. 5;

FIG. 7 is an enlarged view of the indicated area of detail of FIG. 5;

FIG. 11 is a top perspective view of the upper carriage extension bar of the drive bar assembly engaged with the upper carriage drive bars of the drive bar assembly;

FIG. 12 is an enlarged view of indicated area of detail of FIG. 11;

FIG. 13 is an enlarged view of indicated area of detail of FIG. 2;

FIG. 25 is a front perspective view of the stitching end effector of FIG. 2 with the upper jaw and the outer tube removed;

FIG. 26 is an enlarged view of the indicated area of detail of FIG. 25 with the cradles in the retracted configuration and the needles within the needle slots of the lower jaw;

FIG. 30 is a cross-sectional view of the stitching end effector of taken along section line "30-30" of FIG. 16;

FIG. 31 is an enlarged view of the indicated area of detail of FIG. 30;

FIG. 34-38 are a progression of longitudinal side cross-sectional views of the stitching end effector forming first, second, and third stitch loops as the drive bar assembly is manipulated in accordance with the present disclosure.

DETAILED DESCRIPTION

Figure 1:
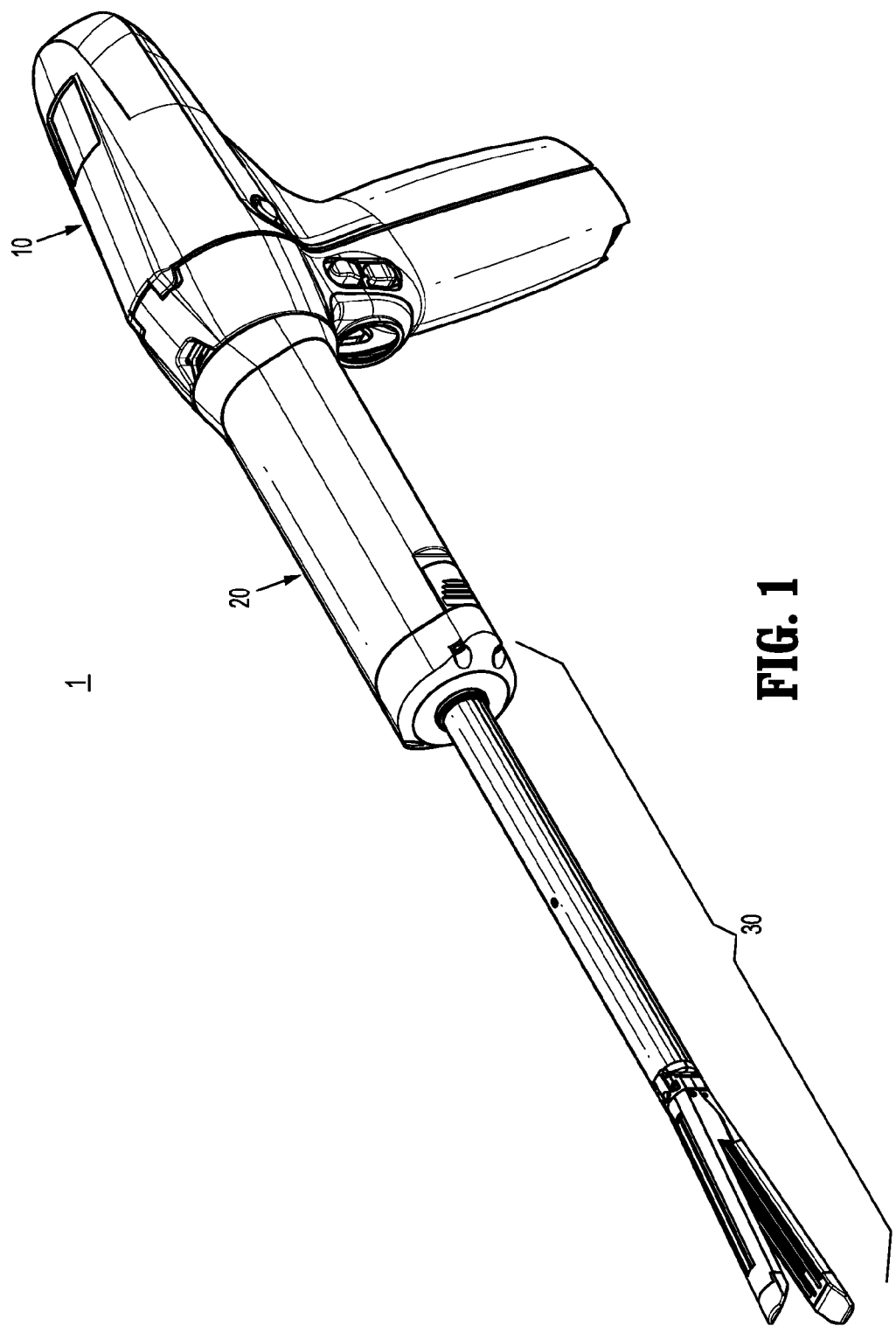
FIG. 1 is a front perspective view of an embodiment of a surgical instrument in accordance with the present disclosure including a stitching end effector.

Embodiments of the present disclosure are now described in detail with reference to the drawings in which like reference numerals designate identical or corresponding elements in each of the several views. As used herein, the term "clinician" refers to a doctor, a nurse, or any other user, operator, or care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, an exemplary embodiment of a surgical instrument 1 is provided in accordance with present disclosure and includes a handle 10, a stitching adaptor 20, and a stitching loading unit 30. The stitching loading unit 30 is configured to provide a line of stitches along the length of a jaw assembly as will be discussed in detail below. The handle 10 is a powered handle with one or more drive shafts (not shown) that rotate independently of one another. An exemplary embodiment of such a powered handle is disclosed in commonly owned and co-pending U.S. patent application Ser. No. 13/484,975 filed May 31, 2012, and now published as U.S. Patent Publication No. 2012/0253329 on Oct. 4, 2012, the contents of which are incorporated herein by reference in its entirety. It is also contemplated that the handle 10 may be a manually driven handle with one or more output shafts.

The stitching adaptor 20 converts rotary motion of the drive shafts of the handle 10 into linear motion of selected drive bars to manipulate the stitching loading unit 30 as detailed below. The stitching adaptor 20 may include one or more gear trains (not shown) and one or more cams to convert the rotary motion of the drive shafts of the handle 10 into linear motion of the drive bars. An exemplary embodiment of such a stitching adaptor 20 is disclosed in commonly owned and co-pending U.S. patent application Ser. No.

14/279,928, filed May 16, 2014, now published as U.S. Patent Publication No. 2015/0327850, the contents of which are incorporated herein by reference in its entirety.

Figure 4:
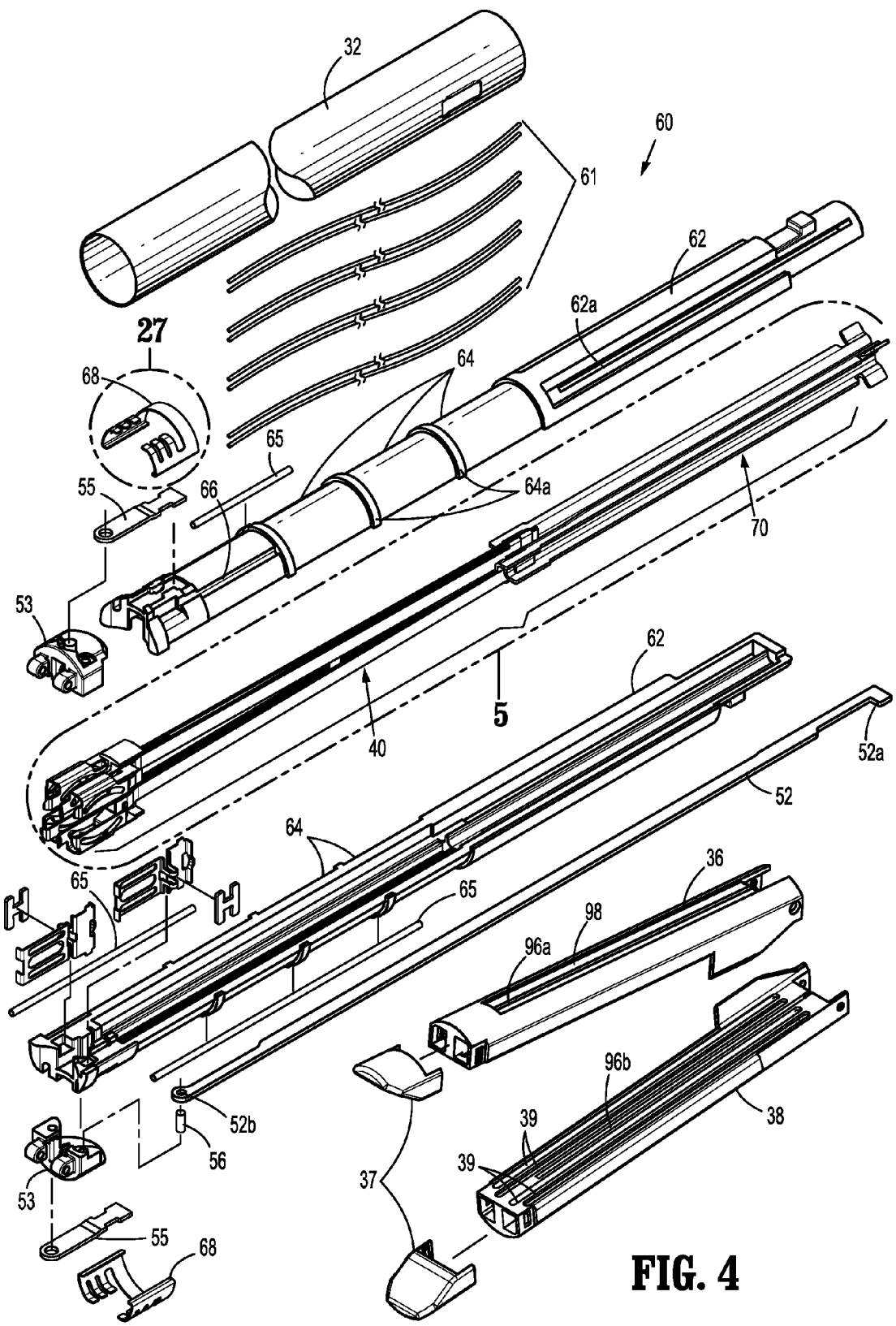
FIG. 4 is an exploded view of the stitching end effector of FIG. 2.
Figure 5:
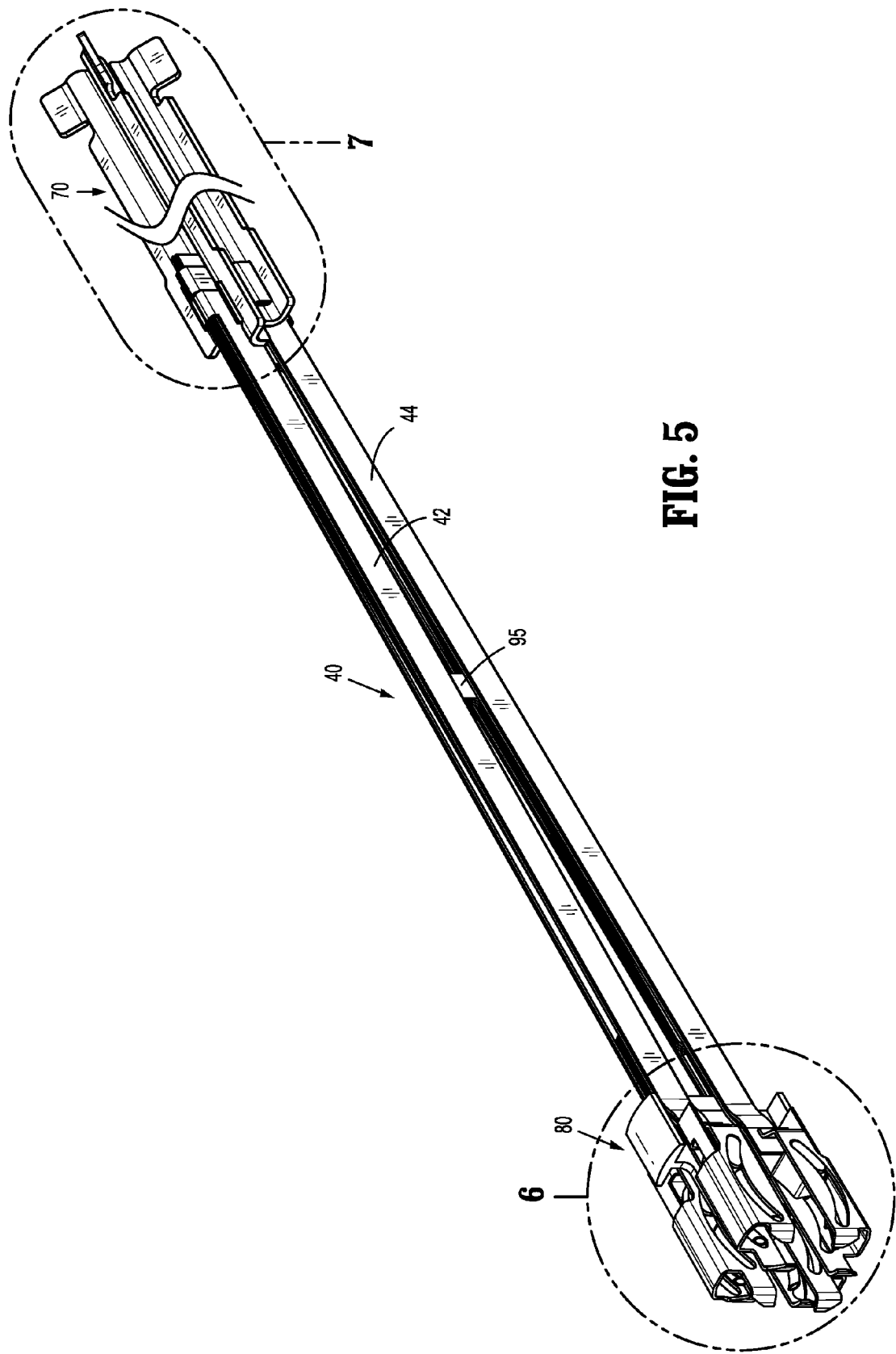
FIG. 5 is an enlarged view of the indicated area of detail of FIG. 4.

With reference to FIGS. 2-4, the stitching loading unit 30 includes an outer tube 32, a jaw assembly 34, and an inner housing 62. A proximal end of the stitching loading unit 30 forms a connector 33 that engages the stitching adaptor 20 to secure the stitching loading unit 30 to the stitching adaptor 20.

Figures 32, 33:
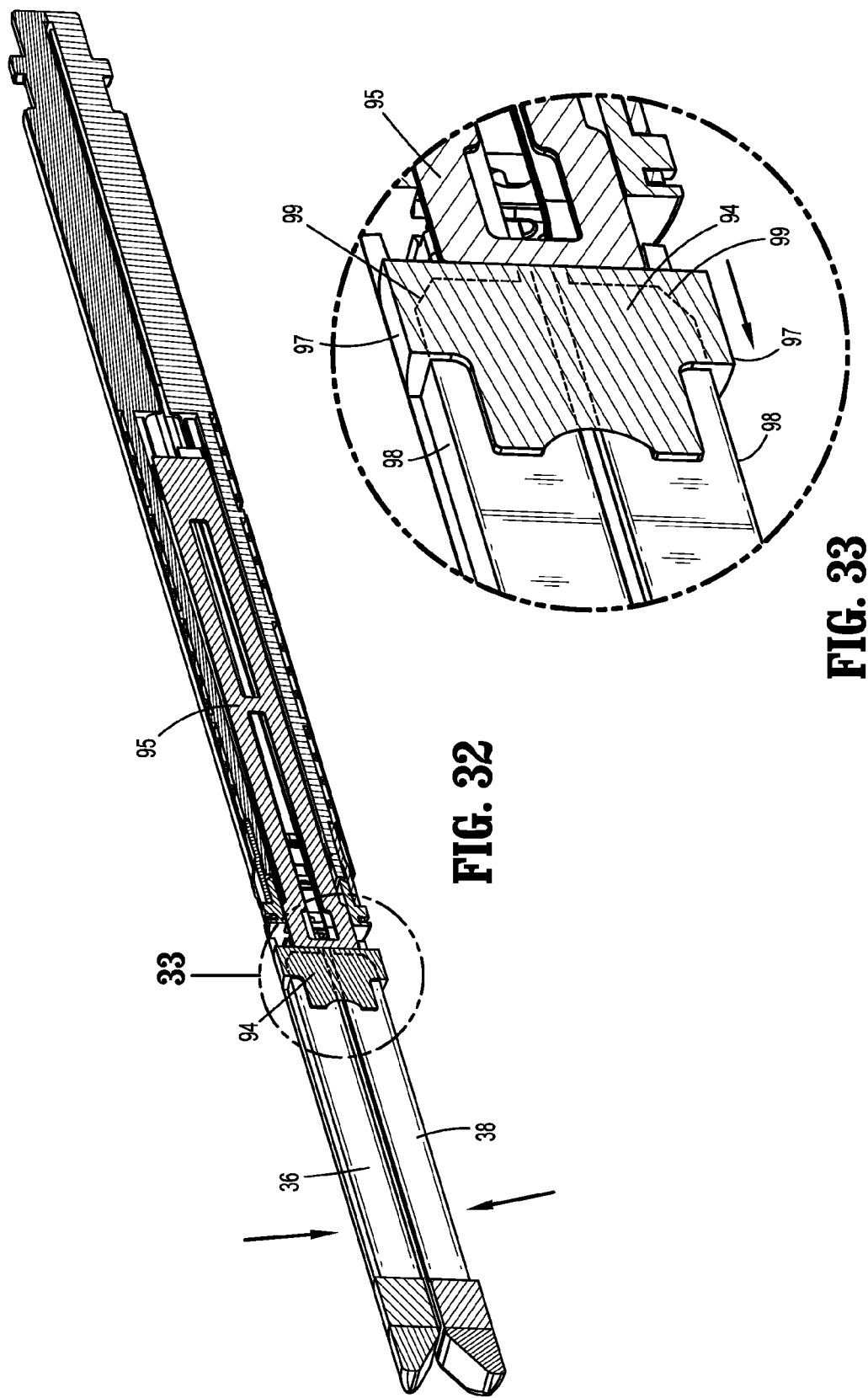
FIG. 32 is a cross-sectional view of the stitching end effector illustrating the drive bar assembly advanced to a clamped position.
FIG. 33 is an enlarged view of the indicated area of detail of FIG. 32.

The jaw assembly 34 includes a first or upper jaw member 36 and a second or lower jaw member 38. The upper and lower jaw members 36, 38 are moveable relative to one another between an open configuration (FIG. 3) and a closed or clamped configuration (FIG. 32). The upper jaw member 36 defines a longitudinal knife slot 96a disposed along a longitudinal axis of the upper jaw member 36. The lower jaw member 38 defines a longitudinal knife slot 96b disposed along a longitudinal axis of the lower jaw member 38. Each of the knife slots 96a, 96b extends through an inner or tissue contacting surface of a respective one of the jaw members 36, 38 and an outer surface of a respective one of the jaw members 36, 38. Each of the knife slots 96a, 96b extends along the longitudinal axis of a respective one of the jaw members 36, 38 from a proximal end thereof to a point adjacent a distal end of the respective jaw member 36, 38. The outer surface of each of the jaw members 36, 38 defines a longitudinal beam groove 98 for receiving an upper or lower flange 97 of an I-beam 94 (FIG. 33) as detailed below. The beam grooves 98 are disposed about the knife slots 96a, 96b and extend from the proximal end of each of the jaw members 36, 38 to the distal end of the knife slots 96a, 96b.

Each of the jaw members 36, 38 further defines longitudinal needle slots 39. The needles slots 39 are disposed in pairs on opposite sides of the knife slots 96a, 96b. The needle slots 39 of the lower jaw member 38 oppose the needle slots (not shown) of the upper jaw member 36. The distal end of each of the jaw members 36, 38 includes a blunt tip 37 and angled guide surface 37a which are configured to atraumatically contact and guide tissue between the jaw members 36, 38.

The inner housing 62 is generally cylindrical and is disposed within the outer tube 32. The inner housing 62 may include an upper segment 62a and a lower segment 62b which are secured together using known fastening techniques (e.g., welding, gluing, etc.). The inner housing 62 slidably receives a drive bar assembly 40 and an extension rod assembly 70.

Figure 8:
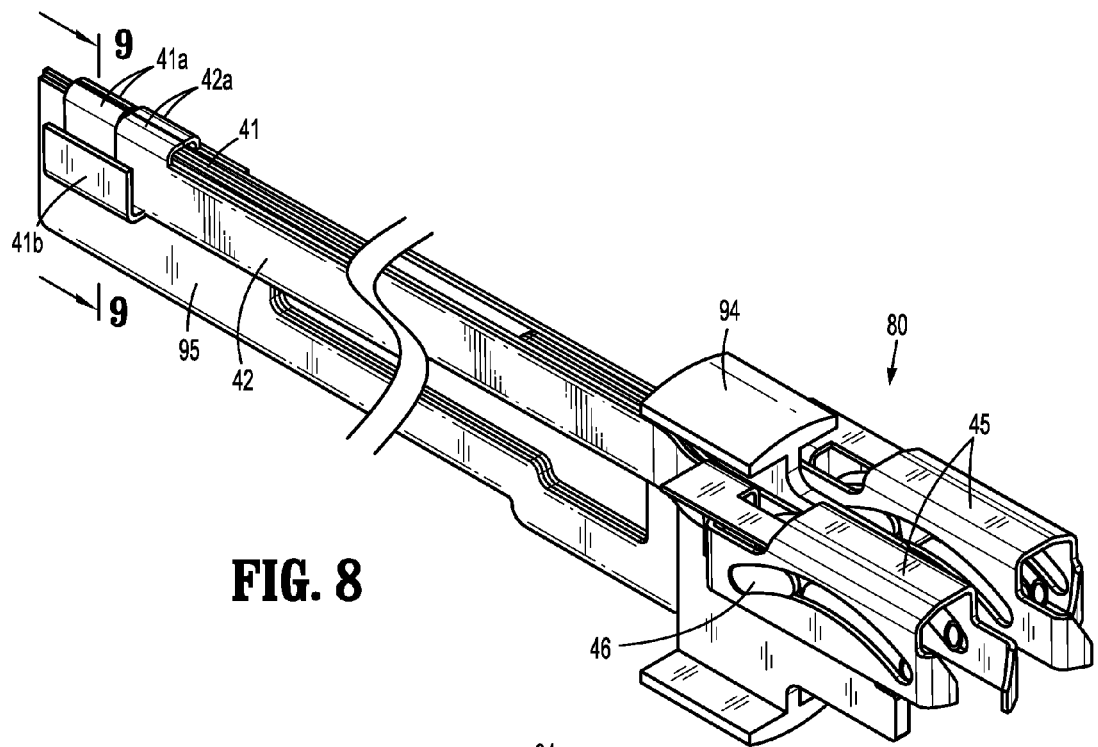
FIG. 8 is a front perspective of the drive bar assembly and the stitching assembly of FIG. 5.
Figure 9:
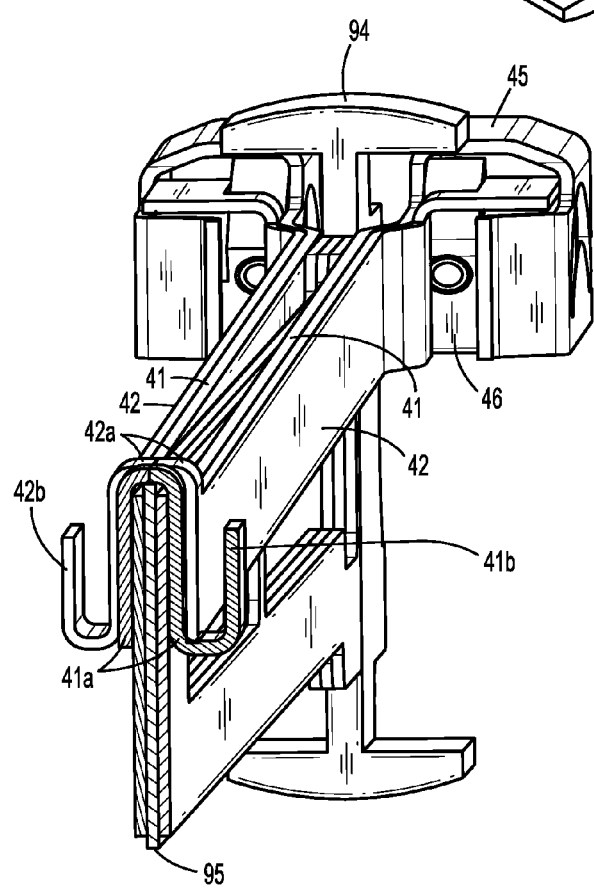
FIG. 9 is a cross-sectional view taken along section line "9-9" of FIG. 8.
Figure 10:
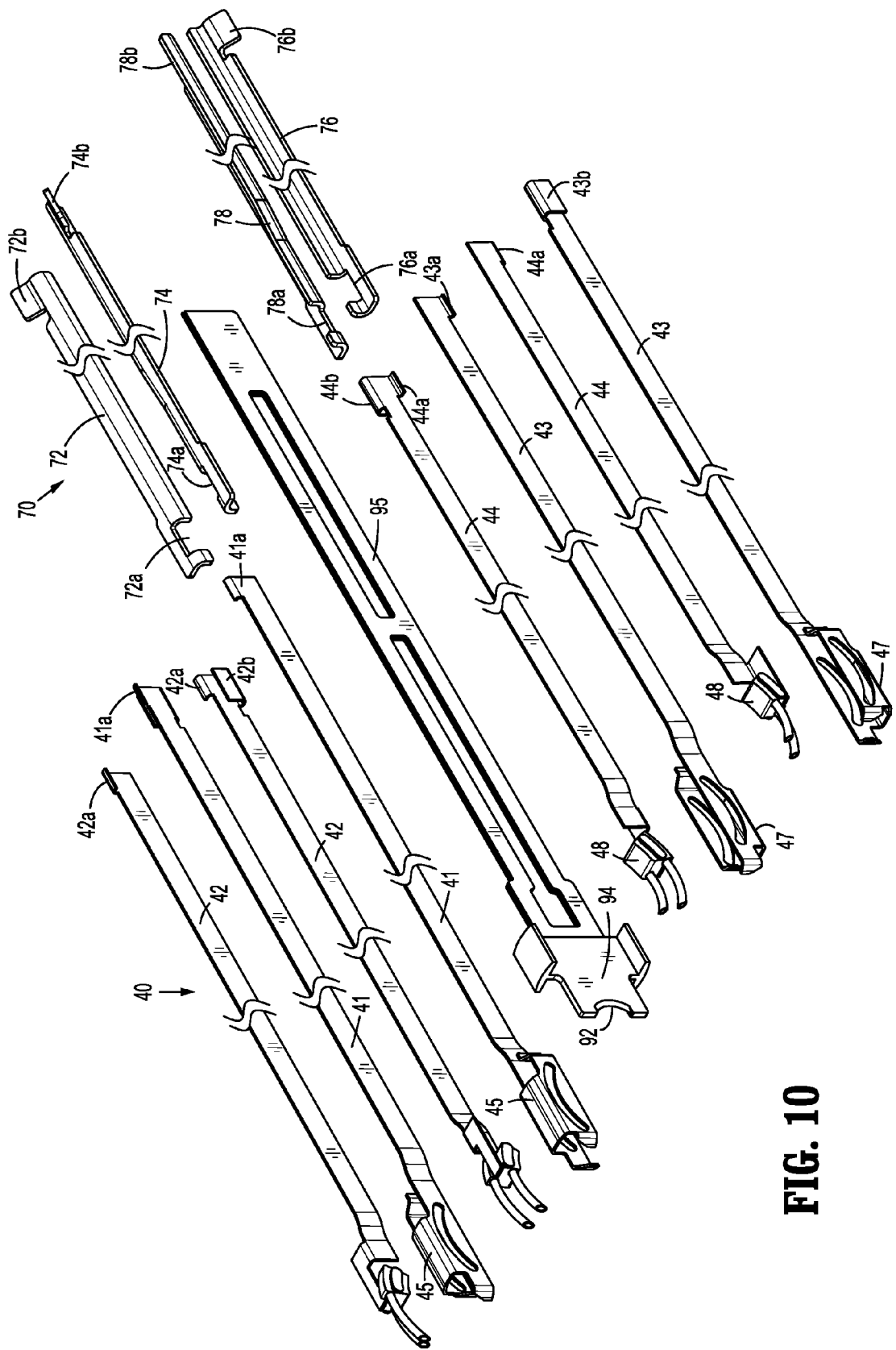
FIG. 10 is an exploded view of the drive bar assembly illustrated in FIG. 5

Referring to FIGS. 5-14, the drive bar assembly 40 includes upper carriage drive bars 41 (FIG. 7), upper cradle drive bars 42 (FIG. 7), lower carriage drive bars 43 (FIG. 10), and lower cradle drive bars 44 (FIG. 10). A stitching assembly 80 (FIG. 6) is supported on a distal end of the drive bar assembly 80 and includes upper carriages 44, upper cradles 45, lower carriages 46, and lower cradles 47. Each of the drive bars 41-44 translate longitudinally in a stepwise manner (i.e., in a series of distinct steps) within the inner housing 62 to actuate the upper carriages 44, upper cradles 45, lower carriages 46, and lower cradles 47 as detailed below.

Each carriage drive bar 41, 43 is positioned adjacent to and flanked by one of the cradle drive bars 42, 44 (FIGS. 9 and 10). A distal end of each of the upper carriage drive bars 41 is connected, either rigidly or releasably, to one of the upper carriages 45 such that longitudinal translation of a drive bar 41 effects longitudinal translation of the upper carriage 45 (FIG. 7). Similarly, a distal end of each of the lower carriage drive bars 43 is connected to one of the lower carriages 47 such that longitudinal translation of a drive bar 41 effects longitudinal translation of the lower carriage 47. In embodiments, the distal end of each of the upper carriage drive bars 41 is integrally formed with one of the upper carriages 45 and the distal end of each of the lower carriage drive bars 43 is integrally formed with one of the lower carriages 47. The carriage drive bars 41, 43 may be connected to corresponding carriages 45, 47 in a rigid or releasable manner, for example integrally formed, snap fit, through glue, welding, molding, or via any variety of fasteners, or any other technique known to those of skill in the art.

The proximal ends 41a of the upper carriage drive bars 41 are connected to one another and the proximal ends 42a of each of the upper cradle drive bars 42 are connected to one another (e.g., by welding or gluing) (FIG. 7). Similarly, the proximal ends 43a (FIG. 14) of each of the lower carriage drive bars 43 are connected to one another and the proximal ends 44a (FIG. 14) of each of the lower cradle drive bars 44 are connected to one another. The proximal ends 41a, 42a, 43a, 44a may be connected to corresponding proximal ends 41a, 42a, 43a, 44a in a rigid or releasable manner, for example integrally formed, snap fit, through glue, welding, molding, or via any variety of fasteners, or any other technique known to those of skill in the art.

The proximal ends 42a of the upper cradle drive bars 42 are positioned distal to the proximal ends 41a of the upper carriage drive bars 41 such that when the upper carriage drive bars 41 are advanced, the proximal ends 41a of the upper carriage drive bars 41 engage the proximal ends 42a of the upper cradle drive bars 42 to advance the upper cradle drive bars 42. Similarly, the proximal ends 44a of the lower cradle drive bars 44 are positioned distal to the proximal ends 43a of the lower carriage drive bars 43 such that when the lower carriage drive bars 43 are advanced, the proximal ends 43a of the lower carriage drive bars 43 engage the proximal ends 44a of the lower cradle drive bars 44 to advance the lower cradle drive bars 44. As shown in FIG. 7, the proximal ends 42a of the upper cradle drive bars 42 may be positioned over the upper carriage drive bars 41. Similarly, the proximal ends 44a of the lower cradle drive bars 44 may be positioned over the lower carriage drive bars 43.

As shown in FIGS. 8 and 9, the upper carriage drive bars 41 are connected to the knife drive member 95 such that longitudinal translation of the upper carriage drive bars 41 effects longitudinal translation of the knife drive member 95. Alternatively, it is contemplated that the lower carriage drive bars 43 may be connected to the knife drive member 95 such longitudinal translation of the lower carriage drive bars 43 effects longitudinal translation of member 95. The carriage drive bars 41, 43 may be connected to the knife drive member 95 in a rigid or releasable manner, for example integrally formed, snap fit, through glue, welding, molding, or via any variety of fasteners, or any other technique known to those of skill in the art.

Figure 14:
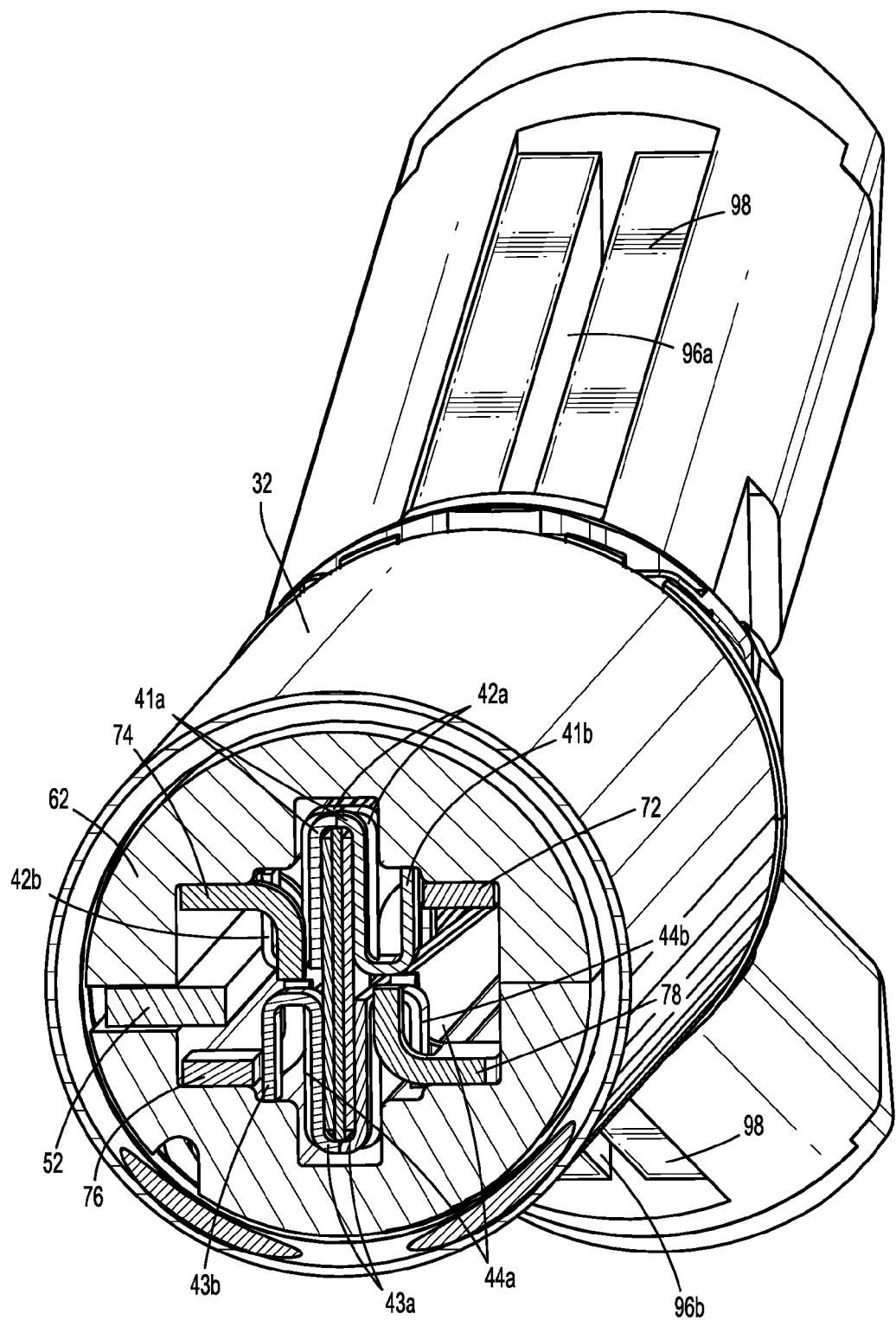
FIG. 14 is a cross-sectional view taken along section line "14-14" of FIG. 2.

The proximal ends 41a of the upper carriage drive bars 41 are connected to an upper carriage drive arm 41b and the proximal ends 42a of the upper cradle drive bars 42 are connected to an upper cradle drive arm 42b (FIG. 9). For example, the upper carriage drive arm 41b may be integrally formed with a proximal end 41a of one of the upper carriage drive bars 41 and the upper cradle drive arm 42b may be integrally formed with the proximal end 42a of one of the upper cradle drive arms 42b. Alternatively, the upper drive arms 41b, 42b may be welded or glued to a respective one of the upper drive bars 41, 42. Similarly, the proximal ends 43a of the lower carriage drive bars 43 are connected to a lower carriage drive arm 43*b* and the proximal ends 44*a* of the lower cradle drive bars 44 are connected to a lower cradle drive arm 44*b* (FIG. 14). The proximal ends 41*a*, 42*a*, 43*a*, 44*a* of the drive bars 41, 42, 43, 44 may be connected to corresponding drive arms 41*b*, 42*b*, 43*b*, 44*b* in a rigid or releasable manner, for example integrally formed, snap fit, through glue, welding, molding, or via any variety of fasteners, or any other technique known to those of skill in the art.

With particular reference to FIGS. 10-14, the extension rod assembly 70 includes an upper carriage extension rod 72, an upper cradle extension rod 74, a lower carriage extension rod 76, and a lower cradle extension rod 78. The distal portion of each of the extension rods 72, 74, 76, 78 is engagable with includes an engagement mechanism, such as notch 72*a*, 74*a*, 76*a*, 78*a*, configured to engage a respective one of the drive arms 41*b*, 42*b*, 43*b*, 44*b* such that movement, for example longitudinal translation, of the extension rods 72, 74, 76, 78 effects movement, for example longitudinal translation, of each of the drive bars 41, 42, 43, 44, respectively. For example, as shown in FIG. 12, the notch 72*a* in the distal portion of the upper cradle extension rod 72 engages the upper carriage drive arm 41*a* to axially fix upper cradle extension rod 72 to the upper carriage drive bar 41. The proximal end of each of the extension rods 72, 74, 76, 78 includes an extension wing 72*b*, 74*b*, 76*b*, 78*b* (FIG. 10) positioned proximal to the proximal end of the outer tube 32 of loading unit 30 (FIG. 1) adjacent the connector 33. The connector 33 is configured to engage the adaptor 20 such that the adaptor 20 can manipulate the extension wings 72*b*, 74*b* 76*b*, 78*b* to operate the loading unit 30. It is contemplated that the connector 33 may engage a handle or robotic controller which is configured to manipulate the extension wings 72*b*, 74*b* 76*b*, 78*b* to operate the loading unit 30.

When the extension rod assembly 70 is assembled within the loading unit 30, the extension rods 72, 74, 76, 78 are slidably disposed within the inner housing 62 of the loading unit 30. The extension wings or tabs 72*b*, 74*b*, 76*b*, 78*b* of the carriage extension rods 72, 74, 76, 78 extend beyond the outer surface of the inner housing 62 (FIG. 13) to facilitate engagement by the adaptor 20 or other controller. It is also contemplated that the loading unit 30 may engage with the adaptor 20 in any manner known to those of skill in the art. For example, the loading unit 30 may engage with the adaptor 20 by a bayonet-type connection, a J-hook type connection, a screw type connection, a spring-detent connection, or any combination thereof. Examples of such connections are disclosed in U.S. patent application Ser. No. 14/279,928, filed May 16, 2014, and U.S. Pat. No. 7,308, 998, the contents of each are incorporated herein by reference in its entirety.

Figure 15:
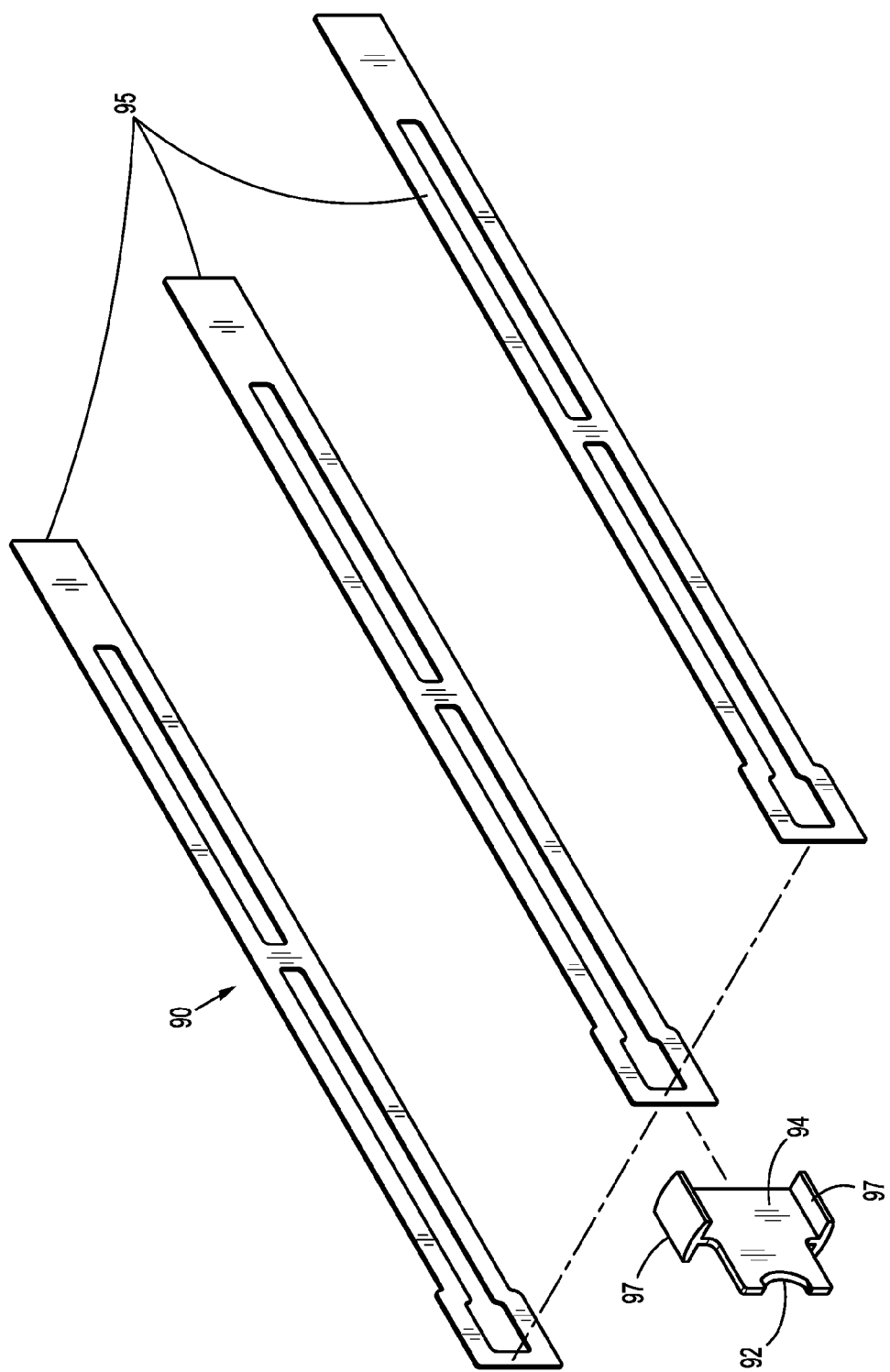
FIG. 15 is an exploded perspective view of the knife assembly.

Referring also to FIG. 15, the knife assembly 90 includes an I-beam 94 and a knife drive member 95. The I-beam 94 has a vertical strut 97*a* defining a knife 92, and upper and lower flanges 97 interconnected by the vertical strut 97*a*. The knife drive member 95 is coupled to a proximal portion of the I-beam 94 to advance and retract the I-beam 94 as detailed below. As detailed above, the knife drive member 95 is connected to the upper carriage drive bars 41 such that the knife drive member 95 is moved, such as advanced and retracted, in response to movement, such as advancement and retraction, of the upper carriage drive bars 41.

Figure 16:
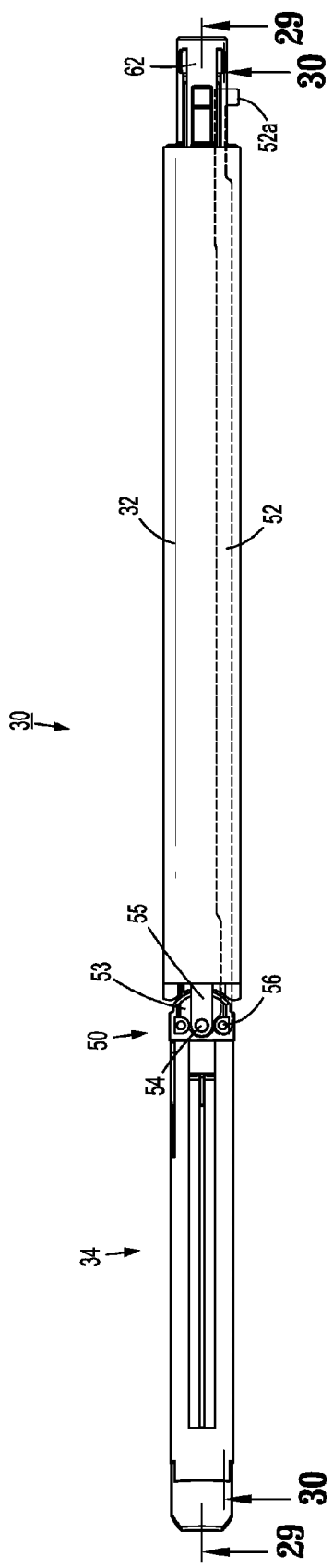
FIG. 16 is a top view of the stitching end effector of FIG. 2 in a non-articulated configuration.
Figure 17:
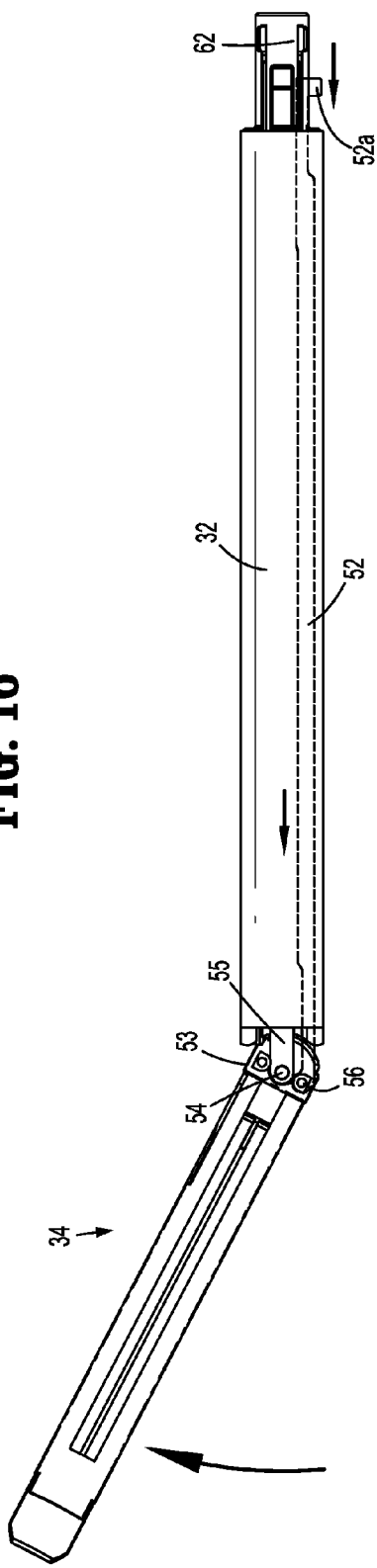
FIG. 17 is a top view of the stitching end effector shown in FIG. 16 in an articulated configuration with a longitudinal axis of the jaw assembly of the end effector defining an angle in relation to a longitudinal axis of the outer tube.
Figure 18:
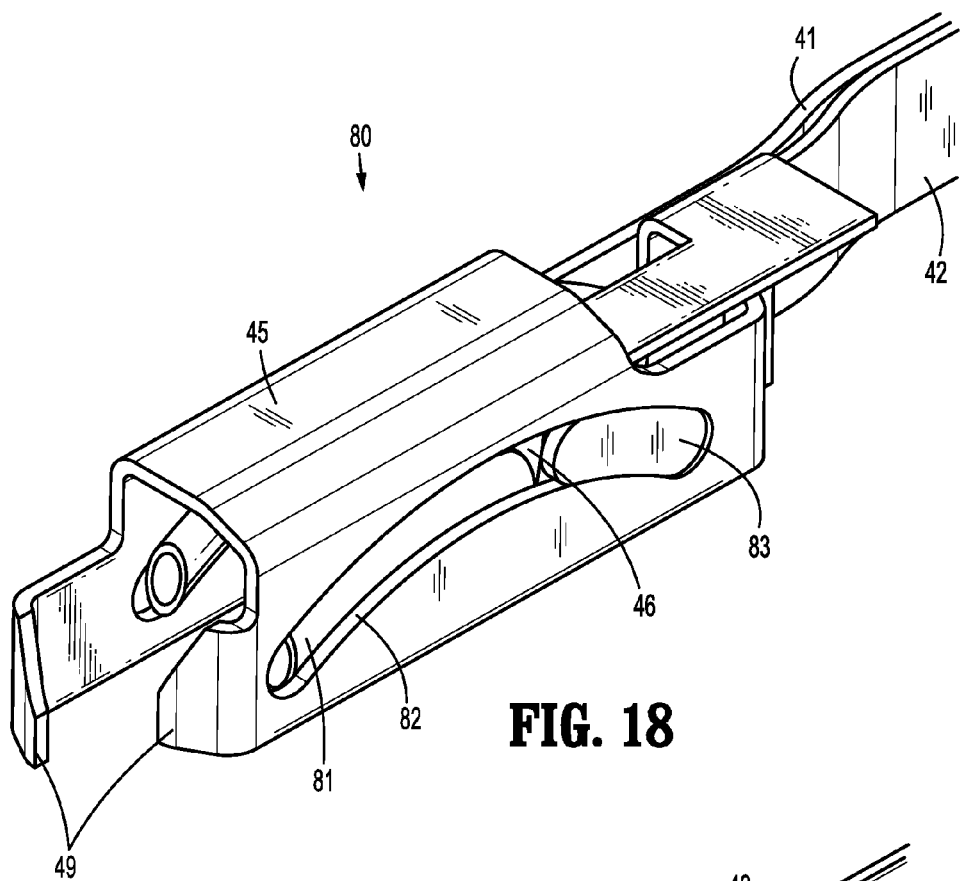
FIG. 18 is an enlarged view of the indicated area of detail of FIG. 10 illustrating the cradle and the carriage of FIG. 10 with the cradle in a retracted configuration.
Figure 28:
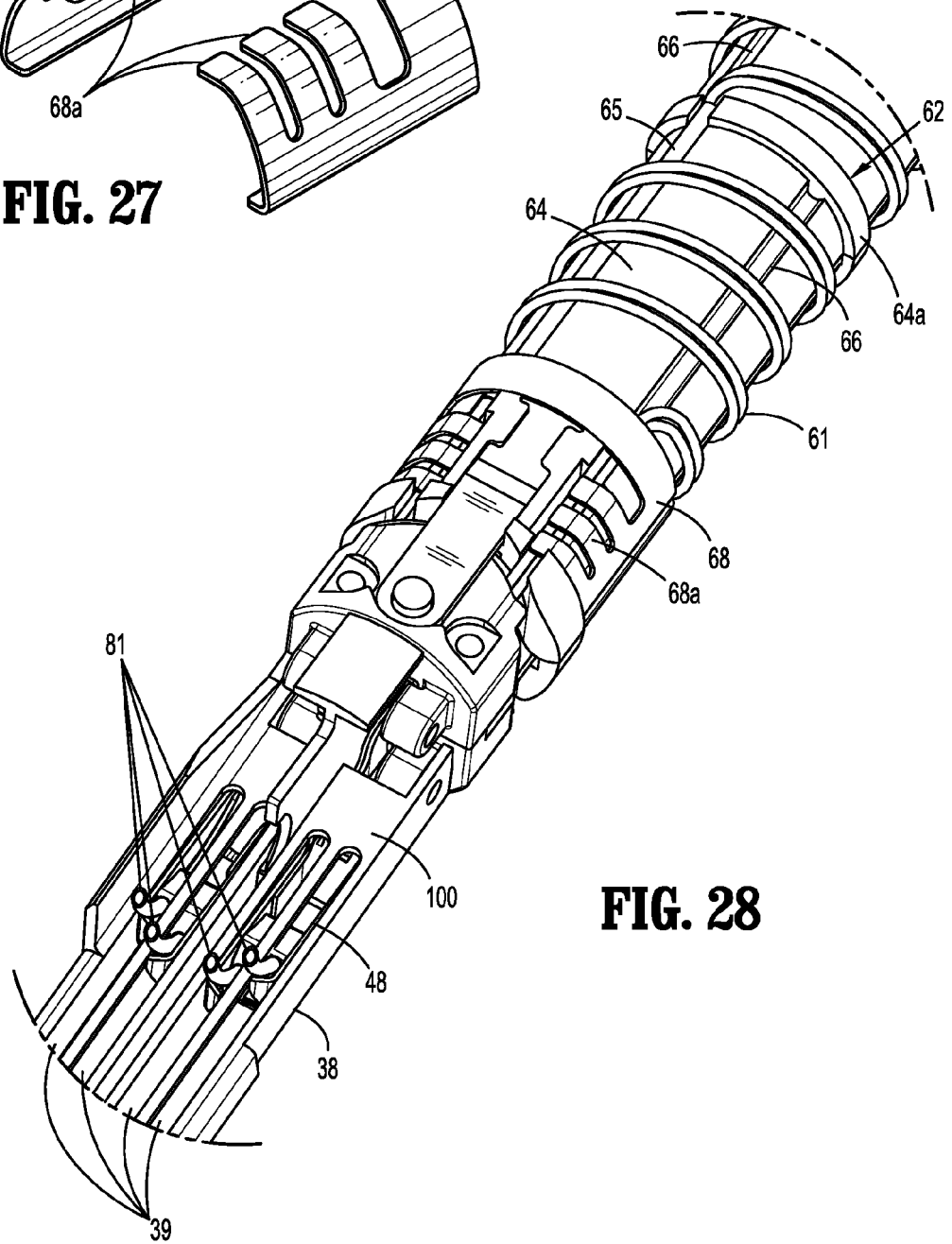
FIG. 28 is a view of the cradles of FIG. 26 in an advanced configuration with the needles extending from the needles slots of the lower jaw.
Figure 29:
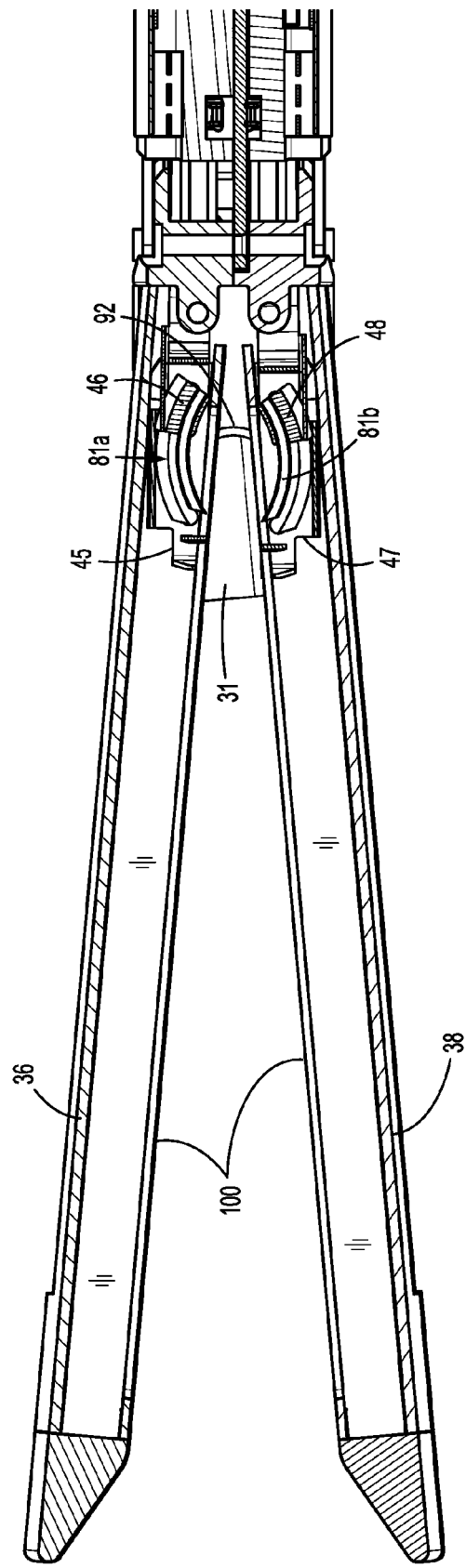
FIG. 29 is a cross-sectional view of the stitching end effector taken along section line "29-29" of FIG. 16.

Referring to FIGS. 16 and 17, the stitching loading unit 30 includes an articulation assembly 50 that includes an articulation member 52, a mounting member 53, an articulation pivot 54, and an articulation pin 56. The articulation assembly 50 is configured to articulate the jaw assembly 34 about an axis perpendicular to a longitudinal axis of the loading unit 30 between a non-articulated configuration (FIG. 16) and an articulated configuration (FIG. 17). The articulation member 52 is slidably disposed within the inner housing 62 and outer tube 32. An articulation bar arm 52*a* is positioned at the proximal end of the articulation member 52 and is engaged by the adaptor 20 to facilitate longitudinal translation of the articulation member 52 upon actuation of the adaptor 20. The distal end of the articulation member 52 includes an opening 52*b* (FIG. 4) that receives the articulation pin 56 (FIG. 2). The articulation pin 56 passes through the opening 52*b* into the mounting member 53. The mounting member 53 is secured to the proximal end of the jaw assembly 34 and is pivotally connected to the inner housing 62 by the articulation pivot 54. As the articulation member 52 is advanced within the inner housing 62, the articulation pin 56, which is offset from the longitudinal axis of the jaw member assembly 34 and articulation pivot 54, pivots mounting member 53 to articulate the jaw assembly 34 (FIG. 28). It is understood that as the articulation member 52 is retracted, the articulation pin 56 will pivot the mounting member 53 in the opposite direction to pivot the jaw assembly 34 in the opposite direction. Each of the carriage drive bars 41, 43, the cradle drive bars 42, 44, and the knife drive member 95 is flexible to facilitate actuation of the loading unit 30 when the jaw assembly 34 is articulated.

Referring now to FIGS. 18-22, operation of the stitching assembly 80 is described in accordance with the present disclosure with an exemplary upper cradle 46 and an exemplary upper carriage 45. As illustrated, an upper carriage drive bar 41 is connected to the upper carriage 45 and an upper cradle drive bar 42 is connected to the upper cradle 46.

Each upper carriage 45 includes a pair of distally located, spaced sidewalls 45*a*. Each of the sidewalls 45*a* defines an at least partially curved or arced cam slot 82. The upper cradle 46 includes curved or arced cams 83 which protrude from each side of the upper cradle 46. The upper cradle 46 defines suture passages 63 (FIG. 20) which extend through the upper cradle 46. A hollow curved or arced needle 81 is secured to the upper cradle 46 adjacent each suture passage 63 such that a suture 61 (FIG. 2) may pass through the suture passage 63 and out a distal end of the needle 81 as detailed below. The arc of the cam slot 82 is substantially similar to the arc of the needles 81. Each cam 83 of the upper cradle 46 is received within a respective cam slot 82. A distal end of the upper carriage 45 defines plows 49. One plow 49 is aligned with a distal end of each of the needles 81. As shown, each cradle 46 may support a pair of needles 81 with a pair of sutures 61 associated with each pair of needles 81 as detailed below.

Figure 19:
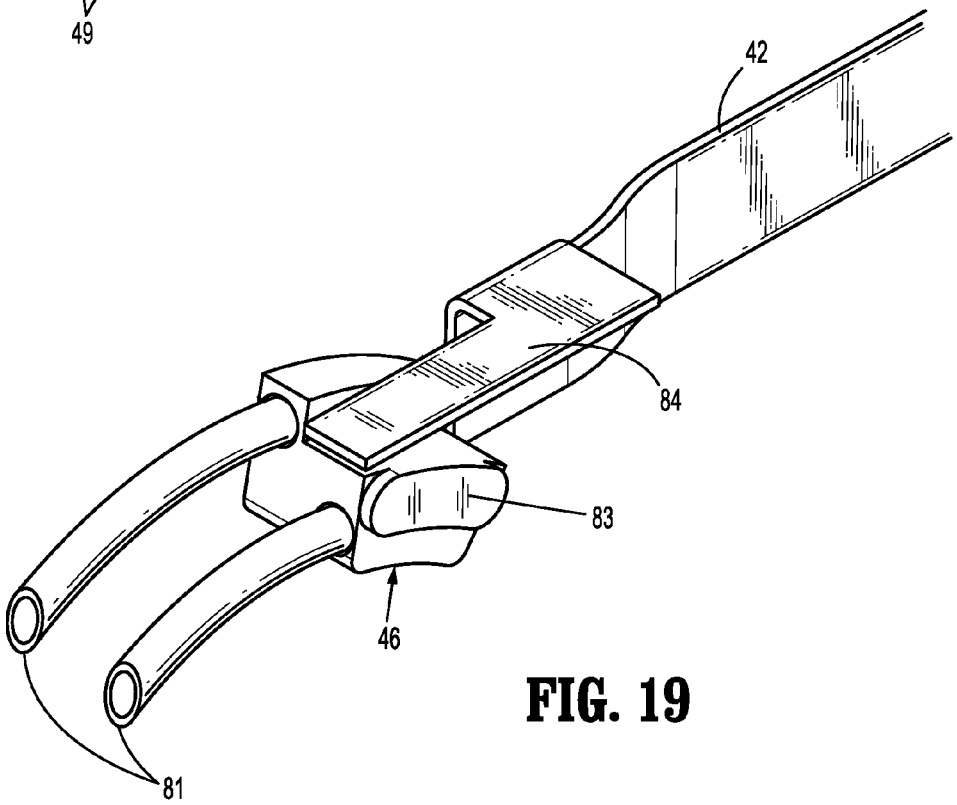
FIG. 19 is a perspective view of the cradle of FIG. 18 with the carriage removed.
Figure 20:
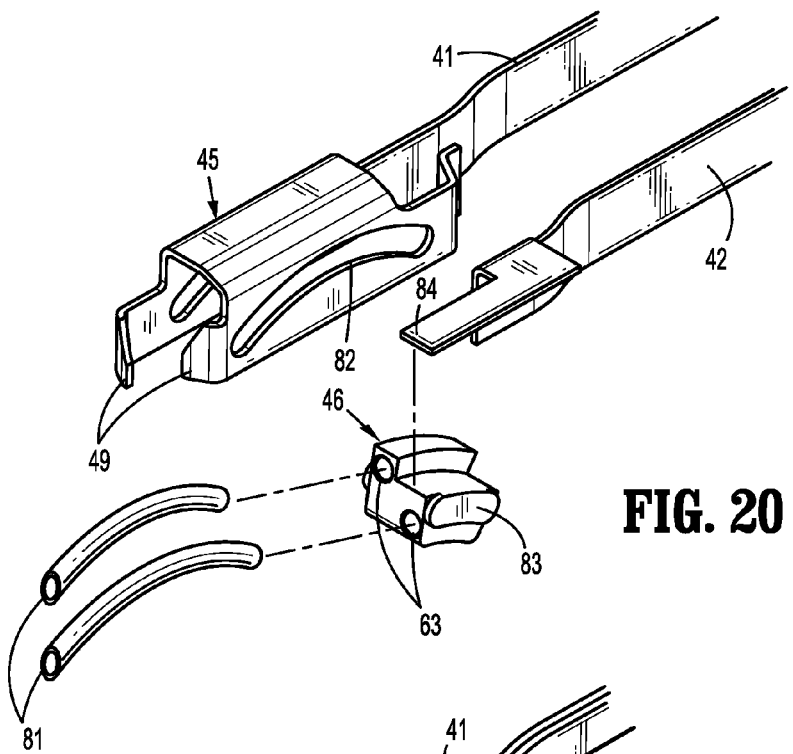
FIG. 20 is an exploded view of the carriage and the cradle of FIG. 18.
Figure 21:
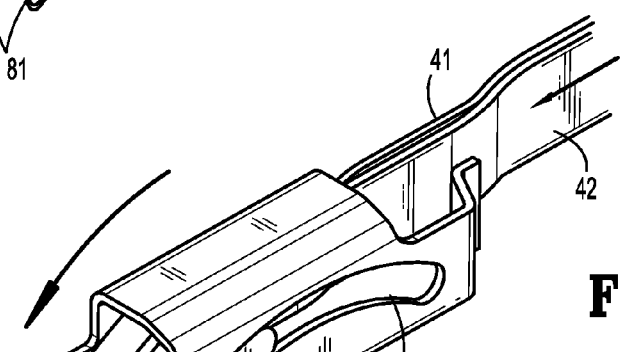
FIG. 21 is a perspective view of the cradle and the carriage of FIG. 18 with the cradle in an advanced configuration.
Figure 22:
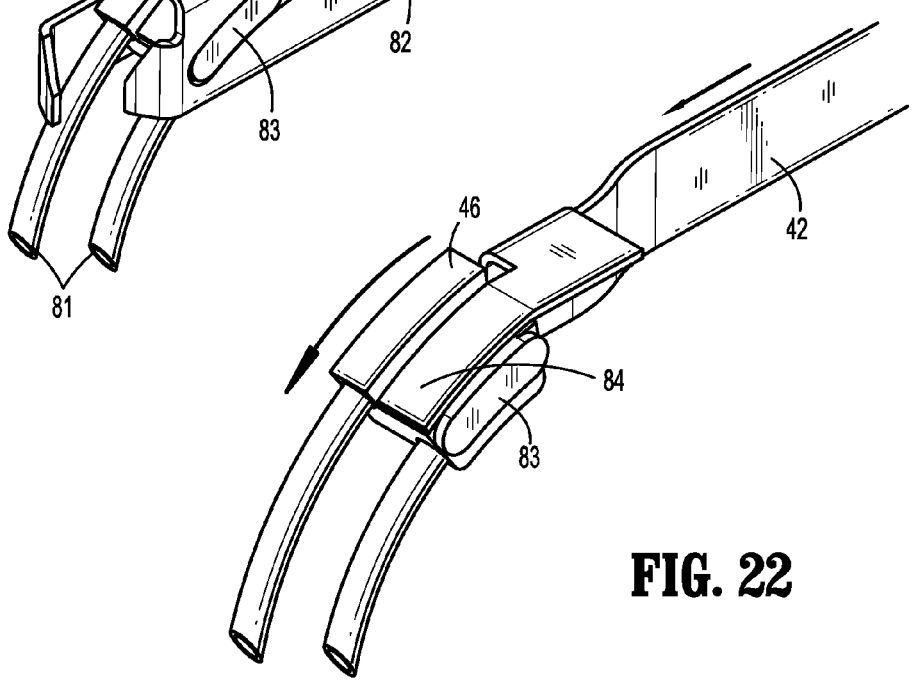
FIG. 22 is a perspective view of the cradle of FIG. 21 with the carriage removed.

The distal end of the upper cradle drive bar 42 includes a cradle drive finger 84 which is operatively associated with the upper cradle 46. The cradle drive finger 84 translates the upper cradle 46 between a retracted configuration (FIGS. 18 and 19) and an advanced configuration (FIGS. 21 and 22). As shown in FIG. 19, the distal end of the cradle drive finger 84 is secured to an upper surface of the upper cradle 46. As the cradle drive bar 42 is advanced to advance the cradle drive finger 84 the cam 83 of the cradle 46 is advanced through the arced cam slot 82. To accommodate the movement of the cradle 46, a portion of the cradle drive finger 84 is curved or flexible to bend as the upper cradle 46 moves through a curved or arched path defined by the arced cam slot 82. When the upper cradle 46 is advanced distally towards the advanced configuration, the cams 83 of the upper cradle 46 translate within the cam slots 82 of the upper carriage 45 to advance the needles 81 along an arced path.

As the needles 81 are advanced in relation to the upper carriage 45 which is held stationary as the upper cradle 46 is advanced, the body of each needle 81 tracks the distal end of the needle 81 such that the body of the needle 81 passes through a hole in tissue created by the distal end of the needle 81. When the needles 81 are retracted in response to retraction of the cradle drive bar 42, the body of each needle 81 passes back through the hole in the tissue such that the distal end of the needle 81 is withdrawn from the tissue. It will be understood, that the lower carriages 47 and lower cradles 48 are manipulated in a similar manner to the upper carriage 45 and the upper cradle 46 described above.

Figure 23:
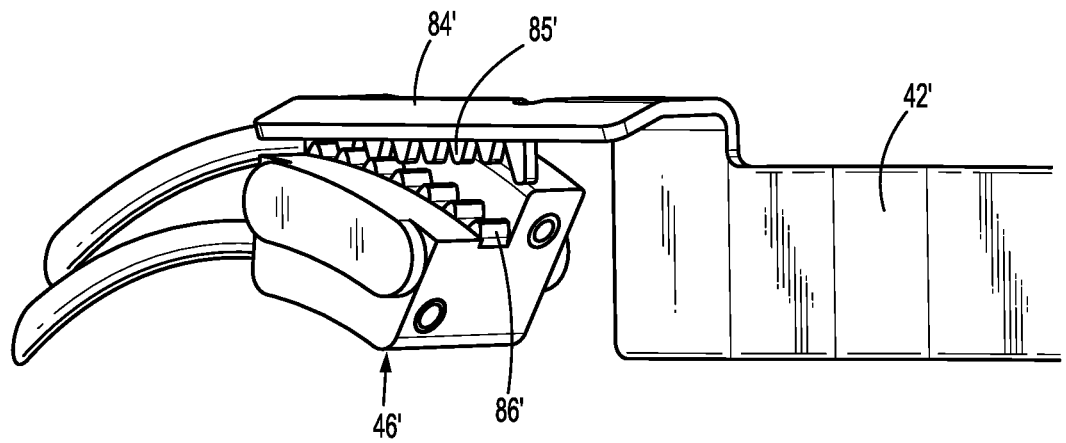
FIG. 23 is perspective view of another embodiment of a cradle drive finger in accordance with the present disclosure including a rack and pinion with the cradle in a retracted configuration.
Figure 24:
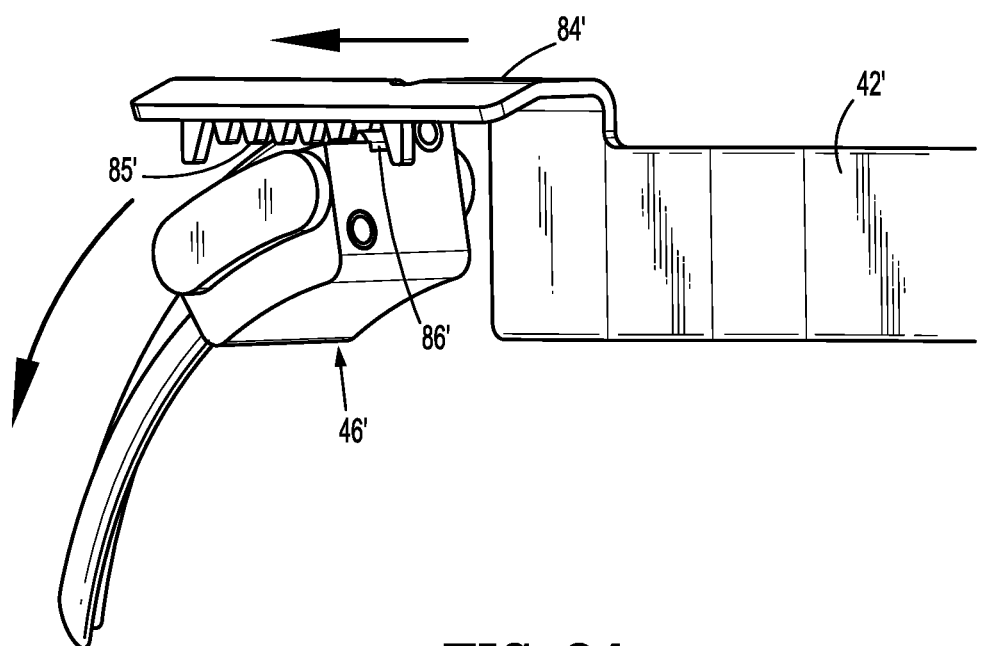
FIG. 24 is a perspective view of the cradle drive finger of FIG. 23 with the cradle in an advanced configuration.

FIGS. 23 and 24 illustrate another embodiment of the presently disclosed cradle drive bar 42' and cradle 46. As illustrated the cradle drive bar 41' includes a cradle drive finger 84' having a toothed rack 85'. The cradle 46' supports a pinion 86' which meshes with the toothed rack 85'. The cradle drive finger 84' is substantially rigid such that as the cradle drive finger 84' is longitudinally translated as a portion of the toothed rack 85' remains engaged with the pinion 86' of the cradle 46' to transition the cradle 46' between the retracted and advanced configurations. It is noted that the cradle 46' is supported by the carriage 45.

With reference to FIGS. 4 and 25-28, the stitching loading unit 30 includes a suture storage and delivery assembly 60 disposed generally between the outer tube 32 and inner housing 62. The suture storage and delivery assembly 60 includes sutures 61 and a suture tensioner 68. The inner housing 62 defines suture recesses 64 which are separated by annular rings 64a. Portions of sutures 61 are wound around the inner housing 62 within the suture recesses 64. The sutures 61 associated with each pair of needles 81 of a respective cradle 46, 48 are stored in pairs in each suture recess 64. The inner housing 62 also defines conduit grooves 66 (FIG. 4) which extend between the suture tensioner 68 and each of the suture recesses 64. A conduit 65 is disposed within each of the conduit grooves 66. A length of the sutures 61 is wound around the inner housing 62 within a suture recess 64, along the conduits 65 and through the suture tensioner 68. The suture tensioner 68 includes tensioning fingers 68a (FIG. 27) that engage the sutures 61 to prevent lengths of sutures 61 from inadvertently being drawn through the suture tensioner 68. In addition, the suture tensioner 68 permits stitch loops to be formed as detailed below. The sutures 61 are fed from the suture tensioner 68, through the suture passages 63 of cradle 46, 48, and through needles 81. The conduits 65 prevent interference between the portion of the sutures 61 wound about the inner housing 62 and the portion of the suture 61 extending through the conduit grooves 65.

When the cradles (e.g., lower cradle 48) are in the retracted position (FIG. 26), the needles 81 associated with the cradle are recessed within the needle slots 39 of a respective jaw member (e.g., lower jaw member 38) beneath a tissue engaging surface 100 of a respective jaw member 36, 38. The sutures 61 extend from the distal end of each needle 81 with a portion positioned along an outer surface of the needles 81. When the needles 81 are advanced from the retracted position to the advanced position (FIG. 25), the needles 81 extend from the needle slots 39 across the tissue engaging surface 100 of the respective jaw member 36, 38 (e.g., lower jaw member 38). As the needles 81 are moved from the retracted position toward the advanced position, a portion of the suture 61 is trapped between the outer surface of the needle 81 and the plow 49 such that as the needle 81 moves an additional portion of sutures 61 are drawn through the suture tensioner 68. Then, as the needles 81 are returned back to the retracted position within the needle slots 39, a loop is formed from a portion of the sutures 61 as detailed below.

Referring to FIGS. 29-38, the operation of the stitching loading unit 30 is detailed in accordance with the present disclosure. In a fully retracted position of the drive bar assembly 40 (FIGS. 29-31) the upper and lower jaws 36, 38 are in an open configuration, the upper and lower cradles 46, 48 are in the retracted position, and the I-beam 94 is in its proximal-most position. The proximal end of the beam grooves 98 include ramps 99 (FIG. 31). In the proximal-most position of the I-beam 94, the flanges 97 of the I-beam 94 are positioned proximal to the ramps 99 of the beam grooves 98. One of the upper and lower jaw members 36, 38 may include a shield 31 (FIG. 29) to prevent premature engagement of tissue with the knife 92.

With tissue (not shown) positioned between the upper and lower jaw members 36, 38, the upper carriage drive bars 41 (FIG. 11) can be longitudinally advanced within the jaw assembly 34 to advance the knife drive member 95. As discussed above, the upper carriage drive bars 41 are engaged with the upper cradle drive bars 42 such that when the upper carriage drive bars 41 are advanced the upper cradle drive bars 42 are also advanced. As the knife drive member 95 is advanced, the knife drive member 95 advances the I-beam 94 to advance the flanges 97 along the beam grooves 98 of the upper and lower jaw members 36, 38 as shown in FIGS. 32 and 33. As the flanges 97 advance into the beam grooves 98, the flanges 97 of the I-beam 94 engage ramps 99 to cam the jaw members 36, 38 to the clamped configuration.

After the upper and lower jaw members 36, 38 are in the clamped configuration, the drive bar assembly 40 (FIG. 10) can be advanced further to translate the carriages 45, 47 and the cradles 46, 48 through the jaw assembly to create stitches with the sutures 61 in tissue clamped between the jaw members 36, 38. The carriages 45, 47 and cradles 46, 48 advance through the jaw assembly in a stepped manner. For example, the carriage 45 and the cradle 46 are advanced together (a first step) to a first suture location. Next, the cradle 46 is advanced and retracted relative to the carriage 45 to move a needle 81 through tissue to apply a suture loop to tissue. Then the carriage 45 and the cradle 46 are advanced together to a second suture location as detailed below. This process is repeated to form suture loops along the length of the jaw assembly 34.

Figure 27:
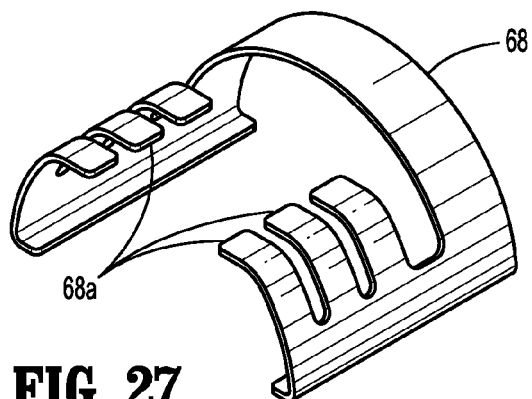
FIG. 27 is an enlarged view of the indicated area of detail of FIG. 4 of the suture tensioner.

Referring to FIG. 34, the upper carriage 45 is advanced, which also advances the upper cradle 46, to a position within the jaw assembly 34. Next, with the upper carriage 45 longitudinally fixed, the upper cradle 46 is advanced to extend needle 81a from the needle slot 39a of the upper jaw member 36, through tissue clamped within the jaw assembly 34, and into the needle slot 39b of the lower jaw member 38. The suture 61a, which passes through needle 81a, is pinched between the plow 49a and the outer surface of needle 81a as the needle 81a is moved such that a length of suture 61a is drawn through the suture tensioner (FIG. 27). As the needle 81 returns to its retracted position, the length of suture 61a forms a first stitch loop 161 (FIG. 35) on the lower side of the tissue clamped within the jaw assembly 34 and adjacent the lower jaw member 38. It is contemplated that a portion of the first stitch loop 161 may be disposed within the needle slot 39b of the lower jaw member 38.

With reference to FIG. 35, when the first stitch loop 161 is formed, the upper cradle 46 is returned to the retracted position within the needle slot 39a of the upper jaw member 36 leaving the first stitch loop 161 on the lower side of tissue clamped within the jaw assembly 34 and adjacent the lower jaw member 38. Next, the lower carriage 47 and the lower cradle 48 are advanced to locate the distal end of the needle 81b of the lower cradle 48 in a position to pass through the first stitch loop 161.

Figure 36:
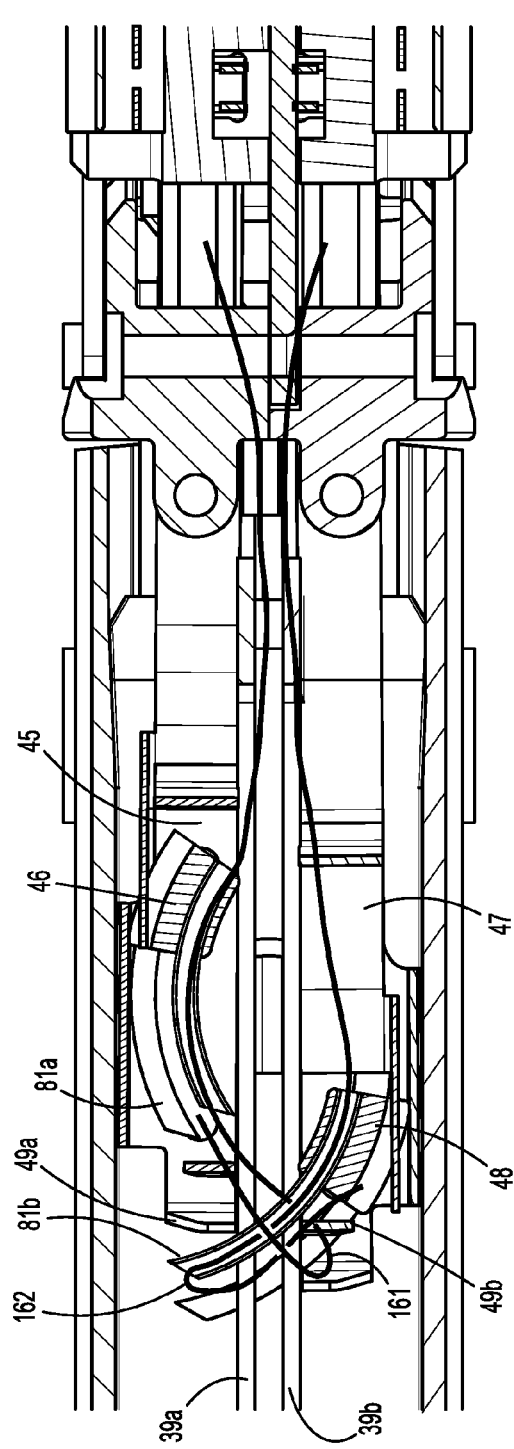

Referring to FIG. 36, with the lower carriage 47 longitudinally fixed, the lower cradle 48 is advanced to extend the needle 81b from the needle slot 39b of the lower jaw member 38, through the first stitch loop 161, through tissue clamped within the jaw assembly, and into the needle slot 39a of the upper jaw member 36. The suture 61b, which passes through needle 81b, is also pinched between the plow 49b and the outer surface of the needle 81b as the needle 81b is extended to draw a length of suture 61b through the suture tensioner (FIG. 27). The length of suture 61b forms a second stitch loop 162 on the upper side of tissue clamped within the jaw assembly 34 distal to the first stitch loop 161 and adjacent the upper jaw member 36.

Figure 37:
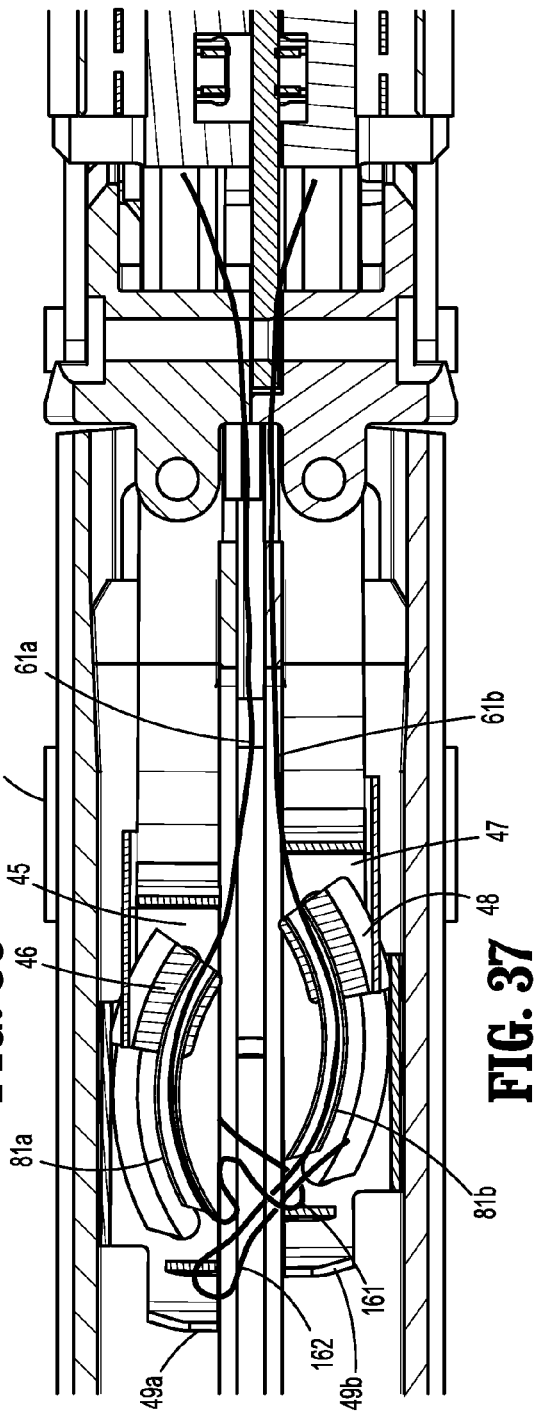

With reference to FIG. 37, when the second stitch loop 162 is formed, the lower cradle 48 is returned to the retracted position within the lower jaw member 38 leaving the second stitch loop 162 on the upper side of tissue clamped within the jaw assembly 34 adjacent the upper jaw member 36. The upper carriage 45 is advanced within the jaw assembly 34 (a second step) to also advance the upper cradle 46 to locate the distal end of needle 81a of the upper cradle 46 in a position to pass through the second stitch loop 162. As the upper carriage 45 is advanced, the knife 92 is advanced to sever tissue clamped within the jaw assembly 34. It will be appreciated that to reduce bleeding, the knife 92 trails the newly formed stitch loops (e.g., stitch loops 161, 162) by at least one stitch loop.

Figure 38:
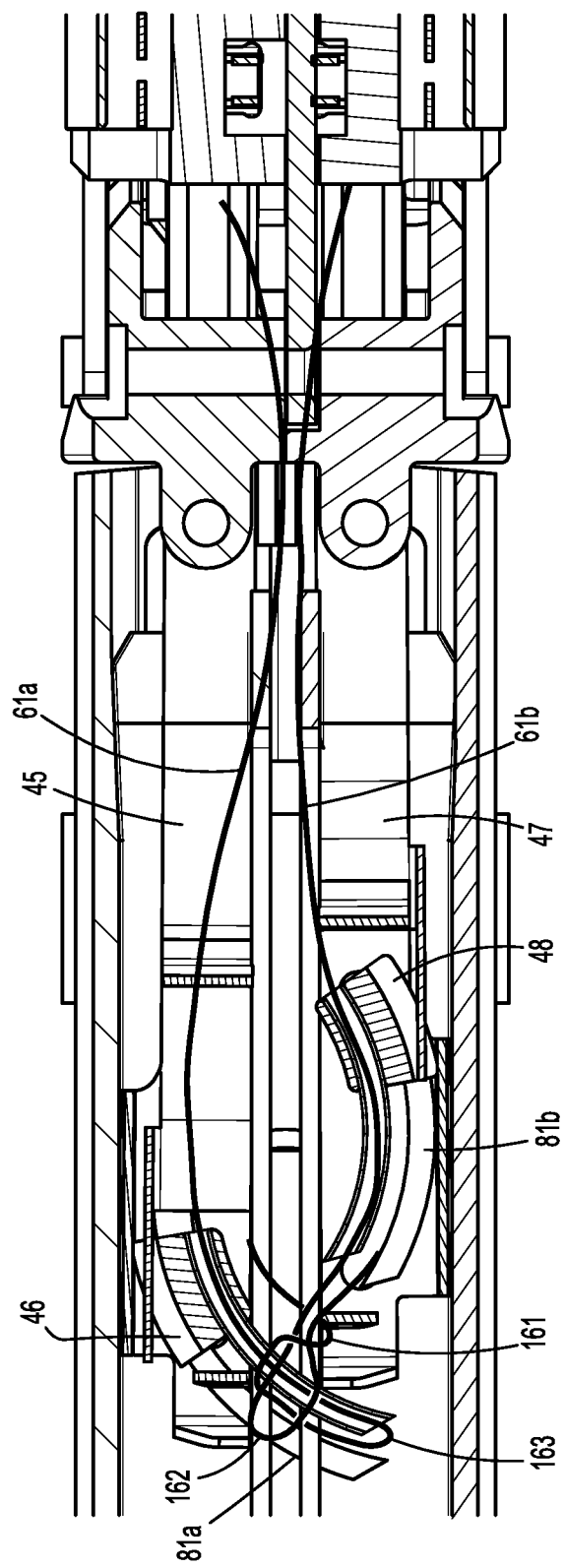

Referring to FIG. 38, with the upper carriage 45 longitudinally fixed, the upper cradle 46 is advanced to extend needle 81a from the needle slot 39a of the upper jaw member 36, through the second stitch loop 162, through tissue clamped within the jaw assembly 34, and into the needle slot 39b of the lower jaw member 38. As discussed above, the suture 61a is pinched between the plow 49a and the outer surface of needle 81a as the needle 81a is extended to tension the first stitch loop 161 on the second stitch loop 162 and to draw an additional length of suture 61a through the suture tensioner 68 (FIG. 27). The additional length of the suture 61a forms a third stitch loop 163 on the lower side of tissue clamped within the jaw assembly 34. The tensioned stitch loops form stitches.

This process is repeated to form additional stitches until the carriages 45, 47 reach the end of the jaw members 36, 38 or until a desired portion of tissue is stitched and cut (e.g., a body lumen is sutured and dissected). To open the jaw members 36, 38, the drive bar assembly 40 is returned to the fully retracted position to withdraw the flanges 97 of the I-beam 94 from the beam grooves 98 releasing the jaw members 36, 38 from the clamped configuration. The suture tensioner 68 maintains tension in the sutures 61 to continuously stitch an additional portion of tissue clamped within the jaw assembly 34. When the desired portion of tissue is stitched and cut, the excess of sutures 61a, 61b is trimmed.

If additional tissue stitching and cutting is required, the jaw assembly 34 is advanced over additional tissue and the process is repeated until the desired portion of tissue is stitched and cut.

It is contemplated that stitching loading unit 30 may define openings in the outer tube 32 proximal to the suture tensioner 68 permitting lengths of the sutures 61 to be stored external to the stitching loading unit 30. It will be understood that storing lengths of the sutures 61 external to the stitching loading unit 30 may permit the stitching loading unit 30 to be used indefinitely.

Although the jaw members 36, 38 of the jaw assembly 34 are illustrated as being substantially linear, it is contemplated that jaw members 36, 38 of jaw assembly 34 may be curved along a length thereof. An exemplary embodiment of such a curved jaw assembly is disclosed in commonly owned U.S. Pat. No. 7,988,028, the contents of which are incorporated herein by reference in its entirety.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An end effector comprising:
    a first cradle;
    a first carriage moveably supporting the first cradle along a first curved path between an advanced position and a retracted position relative to the first carriage;
    a first needle supported by and extending distally from the first cradle;
    a first suture supported by the first needle, the first cradle and the first carriage configured to draw the first suture through tissue when the first cradle moves towards the advanced position and configured to form a first stitch loop in the first suture when the first cradle is moved from the advanced position towards the retracted position;
    a second needle; and
    a second suture supported by the second needle, the second needle configured to draw the second suture through the first stitch loop.

2. The end effector according to claim 1, wherein the first carriage includes a first plow positioned adjacent a distal portion of the first needle, the first plow being configured to capture the first suture against an outer surface of the first needle as the first needle is moved towards the advanced position.

3. The end effector according to claim 1, wherein the first carriage defines a cam slot and the first cradle includes a cam received within the cam slot of the first carriage.

4. The end effector according to claim 3, wherein the first needle is curved.

5. The end effector according to claim 4, wherein the cam slot of the first carriage is curved and defines the first curved path of the first cradle.

6. The end effector according to claim 5, wherein the first curved path has a curvature that corresponds to a curvature of the first needle.

7. The end effector according to claim 1, further comprising:
    a second cradle supporting the second needle such that the second needle extends distally from the second cradle; and
    a second carriage moveably supporting the second cradle along a second curved path between an advanced position and a retracted position relative to the second carriage, the second suture forming a second stitch loop as the second needle is moved from the advanced position towards the retracted position.

8. The end effector according to claim 7, wherein the second carriage includes a second plow positioned adjacent a distal portion of the second needle, the second plow being configured to capture the second suture against an outer surface of the second needle as the second needle is moved towards the advanced position.

9. A loading unit comprising:
an inner housing having proximal and distal portions;
a first jaw member supported by the distal portion of the inner housing and defining a first needle slot extending in a direction parallel to a longitudinal axis of the first jaw member;
a second jaw member supported by the distal portion of the inner housing and defining a second needle slot extending in a direction parallel to a longitudinal axis of the second jaw member, the first and second jaw members moveable relative to one another between an open position and a clamped position;
a first cradle;
a first carriage moveably supporting the first cradle along a curved path between an advanced position and a retracted position relative to the first carriage;
a first needle supported by and extending distally from the first cradle;
a first suture supported by the first needle, the first cradle moveable in relation to the first carriage to advance the first needle from the first needle slot towards the second needle slot and to retract the first needle from the second needle slot back within the first needle slot, the first cradle and the first carriage drawing the first suture through tissue when the first cradle as the first cradle advances and to form a first stitch loop in the first suture when the first cradle is retracted;
a second needle; and
a second suture supported by the second needle, the second needle drawing the second suture through the first stitch loop.

10. The loading unit according to claim 9, wherein the first carriage includes a first plow positioned adjacent a distal portion of the first needle, the first plow being configured to capture the first suture against an outer surface of the first needle as the first needle is advanced towards the second needle slot.

11. The loading unit according to claim 9, further comprising:
a second cradle supporting the second needle such that the second needle extends distally from the second cradle; and
a second carriage moveably supporting the second cradle such that the second needle advances from within the second needle slot towards the second needle slot and retracts the second needle from the first needle slot back within the second needle slot, the second suture forming a second stitch loop as the second needle is retracted.

12. The loading unit according to claim 11, wherein the second carriage includes a second plow positioned adjacent a distal portion of the second needle, the second plow being configured to capture the second suture against an outer surface of the second needle as the second needle is advanced towards the first needle slot.

13. The loading unit according to claim 9, further comprising a suture storage and delivery assembly including:
a suture tensioner;
a first suture recess defined by and along a length of the inner housing proximal to the suture tensioner;
a second suture recess defined by and along a length of the inner housing proximal to the first suture recess;
a groove defined in the inner housing through the first suture recess and into the second suture recess;
a conduit disposed within the groove;
a portion of the first suture being configured to wind around the inner housing in the first suture recess, pass through the suture tensioner, and pass through the first needle; and
a portion of the second suture being configured to wind around the inner housing in the second suture recess, pass through the conduit, pass through the suture tensioner, and pass through the second needle.

14. The loading unit according to claim 9, further comprising a drive bar assembly disposed within the inner housing, the drive bar assembly having:
a first carriage drive bar including a distal portion connected to the first carriage to move the first carriage within the first jaw member; and
a first cradle drive bar including a distal portion operatively associated with the first cradle to advance and retract the first cradle relative to the first carriage.

15. The loading unit according to claim 14, wherein a proximal portion of the first cradle drive bar is disposed over the first carriage drive bar distal to a proximal end of the first carriage drive bar such that the first cradle is advanced with the first carriage.

16. The loading unit according to claim 14, wherein the distal portion of the first cradle drive bar includes a cradle drive finger operatively associated with the first cradle.

17. The loading unit according to claim 16, wherein the cradle drive finger is flexible and a distal portion of the cradle drive finger is fixed to a surface of the first cradle such that when the first cradle is in an advanced position, the cradle drive finger forms an arc with a surface of the first cradle.

18. The loading unit according to claim 16, wherein the cradle drive finger is substantially rigid and includes a toothed rack and a surface of the first cradle includes a pinion, the toothed rack engaging the pinion to move the first cradle between the retracted and advanced positions.

19. The loading unit according to claim 9, further comprising a knife assembly, the knife assembly including:
an I-beam positioned within and longitudinally translatable within a knife slot, the knife slot defined about the longitudinal axis of each of the first and second jaw members, the knife slot extending from a proximal portion of each of the first and second jaw members towards a distal end of each of the first and second jaw members; and
a knife defined by the I-beam.

20. A stitching assembly comprising:
a first jaw member;
a second jaw member;
a first needle moveable in a stepwise manner distally through the first jaw member, the first needle being moveable from a retracted position in which the first needle is disposed within the first jaw member to an advanced position in which the first needle is extended from the first jaw member towards the second jaw member;
a first suture associated with the first needle;
a second needle moveable in a stepwise manner distally within the second jaw member, the second needle being moveable from a retracted position in which the second needle is disposed within the second jaw member to an advanced position in which the second needle is extended from the second jaw member towards the first jaw member; and a second suture associated with the second needle;

a first drive bar configured to, at each step of movement of the first needle, move the first needle from the retracted position to the advanced position and to return the first needle to the retracted position to form a first suture loop in the first suture through tissue and adjacent the second jaw member; and a second drive bar configured to, at each step of movement of the second needle, move the second needle from the retracted position to the advanced position through a suture loop of the first suture and to return the second needle to the retracted position to form a second suture loop in the second suture through tissue and adjacent the first jaw member.

* * * * *